(12) United States Patent
Haas et al.

US011421254B2

(10) Patent No.: US 11,421,254 B2
(45) Date of Patent: Aug. 23, 2022

(54) BIOTECHNOLOGICAL PRODUCTION OF ALCOHOLS AND DERIVATIVES THEREOF

(71) Applicant: Evonik Operations GmbH, Essen (DE)

(72) Inventors: Thomas Haas, Muenster (DE); Oliver Thum, Ratingen (DE); Jan Christoph Pfeffer, Hanau (DE); Philip Engel, Essen (DE); Christian Gehring, Marl (DE); Markus Poetter, Shanghai (CN)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 17/065,341

(22) Filed: Oct. 7, 2020

(65) Prior Publication Data

US 2021/0024967 A1   Jan. 28, 2021

Related U.S. Application Data

(63) Continuation of application No. 14/367,610, filed as application No. PCT/EP2012/075587 on Dec. 14, 2012, now abandoned.

(30) Foreign Application Priority Data

Dec. 22, 2011   (EP) .................................... 11195222

(51) Int. Cl.
| | | |
|---|---|---|
| *C12P 13/00* | (2006.01) | |
| *C12P 7/649* | (2022.01) | |
| *C12P 7/24* | (2006.01) | |
| *C12P 7/04* | (2006.01) | |
| *C12P 7/6436* | (2022.01) | |
| *C12N 9/02* | (2006.01) | |
| *C12P 7/6409* | (2022.01) | |
| *C12N 9/10* | (2006.01) | |

(52) U.S. Cl.
CPC ............ *C12P 13/005* (2013.01); *C12N 9/001* (2013.01); *C12N 9/0071* (2013.01); *C12N 9/0077* (2013.01); *C12N 9/1096* (2013.01); *C12P 7/04* (2013.01); *C12P 7/24* (2013.01); *C12P 7/649* (2013.01); *C12P 7/6409* (2013.01); *C12P 7/6436* (2013.01); *C12P 13/001* (2013.01); *C12Y 114/15003* (2013.01); *C12Y 114/11* (2013.01); *Y02E 50/10* (2013.01)

(58) Field of Classification Search
CPC ....... C12P 7/649; C12P 7/6436; C12P 13/005; C12P 7/6409; C12P 7/04; C12P 13/001; C12P 7/24; Y02E 50/10; C12Y 114/11; C12Y 114/15003; C12N 9/0071; C12N 9/001; C12N 9/1096; C12N 9/0077
See application file for complete search history.

(56) References Cited

U.S. PATENT DOCUMENTS

| | | |
|---|---|---|
| 6,620,970 B2 | 9/2003 | Schiffer et al. |
| 6,639,108 B2 | 10/2003 | Schiffer et al. |
| 6,861,540 B2 | 3/2005 | Herwig et al. |
| 6,878,836 B2 | 4/2005 | Haas et al. |
| 7,030,052 B2 | 4/2006 | Stochniol et al. |
| 7,049,450 B2 | 5/2006 | Hofen et al. |
| 7,091,384 B2 | 8/2006 | Jaeger et al. |
| 7,157,610 B2 | 1/2007 | Hofen et al. |
| 7,195,748 B2 | 3/2007 | Jaeger et al. |
| 7,507,862 B2 | 3/2009 | Stochniol et al. |
| 7,754,778 B2 | 7/2010 | Knott et al. |
| 7,879,938 B2 | 2/2011 | Häger et al. |
| 7,923,225 B2 | 4/2011 | Mueller et al. |
| 8,048,654 B2 * | 11/2011 | Berry ................... C12N 15/79 435/134 |
| 8,216,813 B2 | 7/2012 | Thum et al. |
| 8,349,596 B2 | 1/2013 | Mueller et al. |
| 8,349,907 B2 | 1/2013 | Henning et al. |
| 8,372,595 B2 | 2/2013 | Schaffer et al. |
| 8,378,127 B2 | 2/2013 | Dingerdissen et al. |
| 8,389,249 B2 * | 3/2013 | Hoshino ............... C12N 15/52 435/106 |
| 8,399,658 B2 | 3/2013 | Hengstermann et al. |
| 8,404,470 B2 | 3/2013 | Thum et al. |

(Continued)

FOREIGN PATENT DOCUMENTS

| | | |
|---|---|---|
| CA | 2 709 054 | 6/2009 |
| CN | 101580815 | 11/2009 |

(Continued)

OTHER PUBLICATIONS

Huang et al., A review of separation technologies in current and future biorefineries. Separation and Purification Technol., 2008, vol. 62: 1-21. (Year: 2008).*
Kalscheuer et al., Microdiesel: *Escherichia coli* engineered for fuel production Microbiol., 2006, vol. 152: 25-29-2536. (Year: 2006).*
International Search Report and Written Opinion dated Apr. 15, 2013 in PCT/EP2012/075587.
Gerrit Eggink, et al., "Controlled and Functional Expression of the Pseudomonas oleovorans Alkane Utilizing System in Pseudomonas putida and *Escherichia coli*" Journal of Biological Chemistry, vol. 262, No. 36, XP-002161269, Dec. 25, 1987, pp. 17712-17718.

(Continued)

*Primary Examiner* — Ganapathirama Raghu
(74) *Attorney, Agent, or Firm* — Oblon, McClelland, Maier & Neustadt, L.L.P.

(57) ABSTRACT

A method for oxidizing an alkyl, including a) contacting the alkyl with an aqueous solution comprising a microorganism where the microorganism has a reduced fatty acid degradation capacity compared to its wild type, wherein the fatty acid degradation capacity is reduced by deletion, inhibition or inactivation of a gene encoding an enzyme involved in the β-oxidation pathway; and the microorganism expresses a recombinant alkane oxidase, and b) contacting the aqueous solution from a) with a water-immiscible organic solvent.

20 Claims, 4 Drawing Sheets

Specification includes a Sequence Listing.

(56) References Cited

U.S. PATENT DOCUMENTS

| | | |
|---|---|---|
| 8,445,720 B2 | 5/2013 | Hannen et al. |
| 8,486,677 B2 | 7/2013 | Thum et al. |
| 8,604,227 B2 | 12/2013 | Petrat et al. |
| 8,703,451 B2 | 4/2014 | Haas et al. |
| 8,703,993 B2 | 4/2014 | Hannen et al. |
| 8,796,000 B2 | 8/2014 | Thum et al. |
| 8,809,576 B2 | 8/2014 | Schraven et al. |
| 9,000,223 B2 | 4/2015 | Micoine et al. |
| 9,012,227 B2 | 4/2015 | Karau et al. |
| 9,200,043 B2 | 12/2015 | Potter |
| 2002/0087036 A1 | 7/2002 | Haas et al. |
| 2003/0077768 A1 | 4/2003 | Bramucci |
| 2003/0212298 A1 | 11/2003 | Brasse et al. |
| 2003/0215859 A1 | 11/2003 | Affholter |
| 2005/0176121 A1 | 8/2005 | Takeshita et al. |
| 2010/0068773 A1 | 3/2010 | Marx et al. |
| 2010/0071259 A1 | 3/2010 | Hu et al. |
| 2010/0167360 A1 | 7/2010 | Thum et al. |
| 2010/0190224 A1 | 7/2010 | Poetter et al. |
| 2010/0248325 A1 | 9/2010 | Eckstein et al. |
| 2010/0261237 A1 | 10/2010 | Verseck et al. |
| 2010/0266518 A1 | 10/2010 | Springer et al. |
| 2010/0291644 A1 | 11/2010 | Marx et al. |
| 2010/0324257 A1 | 12/2010 | Karau et al. |
| 2011/0039313 A1 | 2/2011 | Verseck et al. |
| 2011/0118433 A1 | 5/2011 | Pötter et al. |
| 2011/0118504 A1 | 5/2011 | Haas et al. |
| 2011/0162259 A1 | 7/2011 | Gaertner |
| 2011/0171702 A1 | 7/2011 | Reinecke et al. |
| 2011/0251399 A1 | 10/2011 | Dingerdissen et al. |
| 2012/0034665 A1 | 2/2012 | Haas et al. |
| 2012/0041216 A1 | 2/2012 | Sieber et al. |
| 2012/0264182 A1 | 10/2012 | Reinecke et al. |
| 2012/0315366 A1 | 12/2012 | Zehnacker et al. |
| 2013/0035403 A1 | 2/2013 | Schaffer et al. |
| 2013/0052700 A1 | 2/2013 | Poetter et al. |
| 2013/0092233 A1 | 4/2013 | Pawlik et al. |
| 2013/0130319 A1 | 5/2013 | Schaffer et al. |
| 2013/0164797 A1 | 6/2013 | Gielen et al. |
| 2013/0165672 A1 | 6/2013 | Klasovsky et al. |
| 2013/0165685 A1 | 6/2013 | Hannen et al. |
| 2013/0183725 A1 | 7/2013 | Poetter et al. |
| 2013/0245276 A1 | 9/2013 | Klasovsky et al. |
| 2013/0331580 A1 | 12/2013 | Klasovsky et al. |
| 2014/0003921 A1 | 2/2014 | Erhardt et al. |
| 2014/0039223 A1 | 2/2014 | Klasovsky et al. |
| 2014/0054224 A1 | 2/2014 | Erhardt et al. |
| 2014/0120587 A1 | 5/2014 | Haas et al. |
| 2014/0141478 A1 | 5/2014 | Schaffer et al. |
| 2014/0178948 A1 | 6/2014 | Schaffer et al. |
| 2014/0186905 A1 | 7/2014 | Schaffer et al. |
| 2014/0199736 A1 | 7/2014 | Köhler et al. |

FOREIGN PATENT DOCUMENTS

| | | |
|---|---|---|
| WO | WO 03/027301 A1 | 4/2003 |
| WO | WO 2008/148640 A1 | 12/2008 |
| WO | WO 2009/077461 A1 | 6/2009 |
| WO | WO 2010/021711 A1 | 2/2010 |
| WO | WO 2010/062480 A2 | 6/2010 |
| WO | WO 2011/036000 A1 | 3/2011 |
| WO | WO 2013/024111 A1 | 2/2013 |
| WO | WO 2013/024114 A2 | 2/2013 |
| WO | WO 2013/083374 A1 | 6/2013 |
| WO | WO 2013/083412 A1 | 6/2013 |
| WO | WO 2013/124401 A1 | 8/2013 |
| WO | WO 2013/135650 A1 | 9/2013 |
| WO | WO 2013/156454 A1 | 10/2013 |

OTHER PUBLICATIONS

Yangkai Duan, et al., "De novo Biosynthesis of Biodiesel by *Escherichia coli* in Optimized Fed-Batch Cultivation" PLOS One, vol. 6, No. 5, XP 055026594, May 23, 2011, pp. 1-7.

Eric J. Steen, et al., "Microbial production of fatty-acid-derived fuels and chemicals from plant biomass" Nature, vol. 463, No. 7280, XP 055011271, Jan. 28, 2010, 5 pages.

Marcel G. Wubbolts, et al., "Biosynthesis or Synthons in Two-Liquid-Phase Media" Biotechnology and Bioengineering, vol. 52, No. 2, XP-000972414, Oct. 20, 1996, pp. 301-308.

Jan B van Beilen et al., "Expanding the alkane oxygenase toolbox: new enzymes and applications" Current Opinion in Biotechnology, vol. 16, No. 3, XP 004934490, Jun. 1, 2005, pp. 308-314.

Paul Handke, et al. "Application and Engineering of Fatty Acid Biosynthesis in *Escherichia coli* for Advanced Fuels and Chemicals", Metabolic Engineering, vol. 13, 2011, pp. 28-37.

Guo, et al., Protein Tolerance to random Amino Acid Change , PNAS, 2004, vol. 101 (25): 9205-9210.

Alcohol: 18 pages down-loaded from http://www.britanica.com/print/article on May 31, 2016.

A short chain alcohol:2 pages down-loaded from http://www.blocyc.org/compound on May 31, 2016.

OchemPat; http://science.uvu.edu/ochem/index.php/alphebetical/c-d/carboxylic-acid-ester/, 3 pages downloaded dated Sep. 3, 2015.

Broun et al, Catalytic plasticity of fatty acid modification enzymes underlying chemical diversity of plant lipids. Science, 1998, vol. 282: 1315-1317.

Chica et al., Semi-rational approaches to engineering enzyme activity: combining the benefits of directed evolution and rational design. Curr. Opi. Biotechnol., 2005, vol. 16: 378-384.

Devos et al., Practical limits of function prediction. Proteins: Structure, Function and Genetics. 2000, vol. 41: 98-107.

Kimchi-Sarfaty et al., A "Silent" polymorphism in the MDR1 gene changes substrate specificity. Science, 2007, vol. 315: 525-528.

Witkowski et al., Conversion of b-ketoacyl synthase to a Malonyl Decarboxylase by replacement of the active cysteine with glutamine, Biochemistry, 1999., vol. 38: 11650.

Seffernick et al., Melamine deaminase and Atrazine chlorohydrolase: 98 percent identical but functionally different. J. Bacteriol., 2001, vol. 183 (8): 2405-2410.

Sen et al., Developments in directed evolution for improving enzyme functions. Appl. Biochem. Biotechnol., 2007, vol. 143: 212-223.

Whisstock et al., Prediction of protein function from protein sequence. Q. Rev. Biophysics., 2003, vol. 36 (3): 307-340.

Wishart et al., A single mutation converts a novel phosphotyrosine binding domain into a dual-specificity phosphatase. J. Biol. Chem., 1995, vol. 270(45): 26782-26785.

Kisselev L., Polypeptide release factors in prokaryotes and eukaryotes: same function, different structure. Structure, 2002, vol. 10: 8-9.

Lennen et al., A process for microbial hydrocarbon synthesis: Overproduction of fatty acids in *Escherichia coli* and catalytic conversion of alkanes. Biotechnol. Bioeng., 2010, vol. 106(2): 193-202.

Nackley et al., Human Caechol-O-Methytransferase haplotypes modulate protein expression by altering mRNA secondary structure. Science, 2006, vol. 314: 1930-1933.

Suana et al., Silent polymorhisms speak: how they affect pharmacogenomics and the treatment of cancer. Cancer Res., 2007, vol. 67(20): 9609-9612.

\* cited by examiner

SEQUENCE LISTING

<160> NUMBER OF SEQ ID NOS: 20

<210> SEQ ID NO 1
<211> LENGTH: 401
<212> TYPE: PRT
<213> ORGANISM: Pseudomonas putida

<400> SEQUENCE: 1

Met Leu Glu Lys His Arg Val Leu Asp Ser Ala Pro Glu Tyr Val Asp
1               5                   10                  15

Lys Lys Lys Tyr Leu Trp Ile Leu Ser Thr Leu Trp Pro Ala Thr Pro
                20                  25                  30

Met Ile Gly Ile Trp Leu Ala Asn Glu Thr Gly Trp Gly Ile Phe Tyr
            35                  40                  45

Gly Leu Val Leu Leu Val Trp Tyr Gly Ala Leu Pro Leu Leu Asp Ala
        50                  55                  60

Met Phe Gly Glu Asp Phe Asn Asn Pro Pro Glu Glu Val Val Pro Lys
65                  70                  75                  80

```
Leu Glu Lys Glu Arg Tyr Tyr Arg Val Leu Thr Tyr Leu Thr Val Pro
            85                  90                  95

Met His Tyr Ala Ala Leu Ile Val Ser Ala Trp Trp Val Gly Thr Gln
            100                 105                 110

Pro Met Ser Trp Leu Glu Ile Gly Ala Leu Ala Leu Ser Leu Gly Ile
            115                 120                 125

Val Asn Gly Leu Ala Leu Asn Thr Gly His Glu Leu Gly His Lys Lys
            130                 135                 140

Glu Thr Phe Asp Arg Trp Met Ala Lys Ile Val Leu Ala Val Val Gly
145                 150                 155                 160

Tyr Gly His Phe Phe Ile Glu His Asn Lys Gly His His Arg Asp Val
                165                 170                 175

Ala Thr Pro Met Asp Pro Ala Thr Ser Arg Met Gly Glu Ser Ile Tyr
            180                 185                 190

Lys Phe Ser Ile Arg Glu Ile Pro Gly Ala Phe Ile Arg Ala Trp Gly
            195                 200                 205

Leu Glu Glu Gln Arg Leu Ser Arg Arg Gly Gln Ser Val Trp Ser Phe
            210                 215                 220

Asp Asn Glu Ile Leu Gln Pro Met Ile Ile Thr Val Ile Leu Tyr Ala
225                 230                 235                 240

Val Leu Leu Ala Leu Phe Gly Pro Lys Met Leu Val Phe Leu Pro Ile
                245                 250                 255

Gln Met Ala Phe Gly Trp Trp Gln Leu Thr Ser Ala Asn Tyr Ile Glu
            260                 265                 270

His Tyr Gly Leu Leu Arg Gln Lys Met Glu Asp Gly Arg Tyr Glu His
            275                 280                 285

Gln Lys Pro His His Ser Trp Asn Ser Asn His Ile Val Ser Asn Leu
            290                 295                 300

Val Leu Phe His Leu Gln Arg His Ser Asp His His Ala His Pro Thr
305                 310                 315                 320

Arg Ser Tyr Gln Ser Leu Arg Asp Phe Pro Gly Leu Pro Ala Leu Pro
                325                 330                 335

Thr Gly Tyr Pro Gly Ala Phe Leu Met Ala Met Ile Pro Gln Trp Phe
            340                 345                 350

Arg Ser Val Met Asp Pro Lys Val Val Asp Trp Ala Gly Gly Asp Leu
            355                 360                 365

Asn Lys Ile Gln Ile Asp Asp Ser Met Arg Glu Thr Tyr Leu Lys Lys
            370                 375                 380

Phe Gly Thr Ser Ser Ala Gly His Ser Ser Thr Ser Ala Val Ala
385                 390                 395                 400

Ser

<210> SEQ ID NO 2
<211> LENGTH: 448
<212> TYPE: PRT
<213> ORGANISM: Escherichia coli

<400> SEQUENCE: 2

Met Val Met Ser Gln Lys Thr Leu Phe Thr Lys Ser Ala Leu Ala Val
1               5                   10                  15

Ala Val Ala Leu Ile Ser Thr Gln Ala Trp Ser Ala Gly Phe Gln Leu
            20                  25                  30

Asn Glu Phe Ser Ser Ser Gly Leu Gly Arg Ala Tyr Ser Gly Glu Gly
            35                  40                  45
```

Ala Ile Ala Asp Asp Ala Gly Asn Val Ser Arg Asn Pro Ala Leu Ile
            50                  55                  60

Thr Met Phe Asp Arg Pro Thr Phe Ser Ala Gly Ala Val Tyr Ile Asp
 65                  70                  75                  80

Pro Asp Val Asn Ile Ser Gly Thr Ser Pro Ser Gly Arg Ser Leu Lys
                 85                  90                  95

Ala Asp Asn Ile Ala Pro Thr Ala Trp Val Pro Asn Met His Phe Val
            100                 105                 110

Ala Pro Ile Asn Asp Gln Phe Gly Trp Gly Ala Ser Ile Thr Ser Asn
        115                 120                 125

Tyr Gly Leu Ala Thr Glu Phe Asn Asp Thr Tyr Ala Gly Gly Ser Val
    130                 135                 140

Gly Gly Thr Thr Asp Leu Glu Thr Met Asn Leu Asn Leu Ser Gly Ala
145                 150                 155                 160

Tyr Arg Leu Asn Asn Ala Trp Ser Phe Gly Leu Gly Phe Asn Ala Val
                165                 170                 175

Tyr Ala Arg Ala Lys Ile Glu Arg Phe Ala Gly Asp Leu Gly Gln Leu
            180                 185                 190

Val Ala Gly Gln Ile Met Gln Ser Pro Ala Gly Gln Thr Gln Gln Gly
        195                 200                 205

Gln Ala Leu Ala Ala Thr Ala Asn Gly Ile Asp Ser Asn Thr Lys Ile
    210                 215                 220

Ala His Leu Asn Gly Asn Gln Trp Gly Phe Gly Trp Asn Ala Gly Ile
225                 230                 235                 240

Leu Tyr Glu Leu Asp Lys Asn Asn Arg Tyr Ala Leu Thr Tyr Arg Ser
                245                 250                 255

Glu Val Lys Ile Asp Phe Lys Gly Asn Tyr Ser Ser Asp Leu Asn Arg
            260                 265                 270

Ala Phe Asn Asn Tyr Gly Leu Pro Ile Pro Thr Ala Thr Gly Gly Ala
        275                 280                 285

Thr Gln Ser Gly Tyr Leu Thr Leu Asn Leu Pro Glu Met Trp Glu Val
    290                 295                 300

Ser Gly Tyr Asn Arg Val Asp Pro Gln Trp Ala Ile His Tyr Ser Leu
305                 310                 315                 320

Ala Tyr Thr Ser Trp Ser Gln Phe Gln Gln Leu Lys Ala Thr Ser Thr
                325                 330                 335

Ser Gly Asp Thr Leu Phe Gln Lys His Glu Gly Phe Lys Asp Ala Tyr
            340                 345                 350

Arg Ile Ala Leu Gly Thr Thr Tyr Tyr Asp Asp Asn Trp Thr Phe
        355                 360                 365

Arg Thr Gly Ile Ala Phe Asp Asp Ser Pro Val Pro Ala Gln Asn Arg
    370                 375                 380

Ser Ile Ser Ile Pro Asp Gln Asp Arg Phe Trp Leu Ser Ala Gly Thr
385                 390                 395                 400

Thr Tyr Ala Phe Asn Lys Asp Ala Ser Val Asp Val Gly Val Ser Tyr
                405                 410                 415

Met His Gly Gln Ser Val Lys Ile Asn Glu Gly Pro Tyr Gln Phe Glu
            420                 425                 430

Ser Glu Gly Lys Ala Trp Leu Phe Gly Thr Asn Phe Asn Tyr Ala Phe
        435                 440                 445

<210> SEQ ID NO 3
<211> LENGTH: 561

<212> TYPE: PRT
<213> ORGANISM: Escherichia coli

<400> SEQUENCE: 3

Met Lys Lys Val Trp Leu Asn Arg Tyr Pro Ala Asp Val Pro Thr Glu
1               5                   10                  15

Ile Asn Pro Asp Arg Tyr Gln Ser Leu Val Asp Met Phe Glu Gln Ser
            20                  25                  30

Val Ala Arg Tyr Ala Asp Gln Pro Ala Phe Val Asn Met Gly Glu Val
        35                  40                  45

Met Thr Phe Arg Lys Leu Glu Glu Arg Ser Arg Ala Phe Ala Ala Tyr
    50                  55                  60

Leu Gln Gln Gly Leu Gly Leu Lys Lys Gly Asp Arg Val Ala Leu Met
65                  70                  75                  80

Met Pro Asn Leu Leu Gln Tyr Pro Val Ala Leu Phe Gly Ile Leu Arg
                85                  90                  95

Ala Gly Met Ile Val Val Asn Val Asn Pro Leu Tyr Thr Pro Arg Glu
            100                 105                 110

Leu Glu His Gln Leu Asn Asp Ser Gly Ala Ser Ala Ile Val Ile Val
        115                 120                 125

Ser Asn Phe Ala His Thr Leu Glu Lys Val Val Asp Lys Thr Ala Val
130                 135                 140

Gln His Val Ile Leu Thr Arg Met Gly Asp Gln Leu Ser Thr Ala Lys
145                 150                 155                 160

Gly Thr Val Val Asn Phe Val Val Lys Tyr Ile Lys Arg Leu Val Pro
                165                 170                 175

Lys Tyr His Leu Pro Asp Ala Ile Ser Phe Arg Ser Ala Leu His Asn
            180                 185                 190

Gly Tyr Arg Met Gln Tyr Val Lys Pro Glu Leu Val Pro Glu Asp Leu
        195                 200                 205

Ala Phe Leu Gln Tyr Thr Gly Gly Thr Thr Gly Val Ala Lys Gly Ala
    210                 215                 220

Met Leu Thr His Arg Asn Met Leu Ala Asn Leu Glu Gln Val Asn Ala
225                 230                 235                 240

Thr Tyr Gly Pro Leu Leu His Pro Gly Lys Glu Leu Val Val Thr Ala
                245                 250                 255

Leu Pro Leu Tyr His Ile Phe Ala Leu Thr Ile Asn Cys Leu Leu Phe
            260                 265                 270

Ile Glu Leu Gly Gly Gln Asn Leu Leu Ile Thr Asn Pro Arg Asp Ile
        275                 280                 285

Pro Gly Leu Val Lys Glu Leu Ala Lys Tyr Pro Phe Thr Ala Ile Thr
    290                 295                 300

Gly Val Asn Thr Leu Phe Asn Ala Leu Leu Asn Asn Lys Glu Phe Gln
305                 310                 315                 320

Gln Leu Asp Phe Ser Ser Leu His Leu Ser Ala Gly Gly Gly Met Pro
                325                 330                 335

Val Gln Gln Val Val Ala Glu Arg Trp Val Lys Leu Thr Gly Gln Tyr
            340                 345                 350

Leu Leu Glu Gly Tyr Gly Leu Thr Glu Cys Ala Pro Leu Val Ser Val
        355                 360                 365

Asn Pro Tyr Asp Ile Asp Tyr His Ser Gly Ser Ile Gly Leu Pro Val
    370                 375                 380

Pro Ser Thr Glu Ala Lys Leu Val Asp Asp Asp Asn Glu Val Pro
385                 390                 395                 400

```
Pro Gly Gln Pro Gly Glu Leu Cys Val Lys Gly Pro Gln Val Met Leu
                405                 410                 415

Gly Tyr Trp Gln Arg Pro Asp Ala Thr Asp Glu Ile Ile Lys Asn Gly
            420                 425                 430

Trp Leu His Thr Gly Asp Ile Ala Val Met Asp Glu Glu Gly Phe Leu
        435                 440                 445

Arg Ile Val Asp Arg Lys Lys Asp Met Ile Leu Val Ser Gly Phe Asn
    450                 455                 460

Val Tyr Pro Asn Glu Ile Glu Asp Val Val Met Gln His Pro Gly Val
465                 470                 475                 480

Gln Glu Val Ala Ala Val Gly Val Pro Ser Gly Ser Ser Gly Glu Ala
                485                 490                 495

Val Lys Ile Phe Val Val Lys Lys Asp Pro Ser Leu Thr Glu Glu Ser
            500                 505                 510

Leu Val Thr Phe Cys Arg Arg Gln Leu Thr Gly Tyr Lys Val Pro Lys
        515                 520                 525

Leu Val Glu Phe Arg Asp Glu Leu Pro Lys Ser Asn Val Gly Lys Ile
    530                 535                 540

Leu Arg Arg Glu Leu Arg Asp Glu Ala Arg Gly Lys Val Asp Asn Lys
545                 550                 555                 560

Ala

<210> SEQ ID NO 4
<211> LENGTH: 814
<212> TYPE: PRT
<213> ORGANISM: Escherichia coli

<400> SEQUENCE: 4

Met Met Ile Leu Ser Ile Leu Ala Thr Val Val Leu Leu Gly Ala Leu
1               5                   10                  15

Phe Tyr His Arg Val Ser Leu Phe Ile Ser Ser Leu Ile Leu Leu Ala
                20                  25                  30

Trp Thr Ala Ala Leu Gly Val Ala Gly Leu Trp Ser Ala Trp Val Leu
            35                  40                  45

Val Pro Leu Ala Ile Ile Leu Val Pro Phe Asn Phe Ala Pro Met Arg
        50                  55                  60

Lys Ser Met Ile Ser Ala Pro Val Phe Arg Gly Phe Arg Lys Val Met
65                  70                  75                  80

Pro Pro Met Ser Arg Thr Glu Lys Glu Ala Ile Asp Ala Gly Thr Thr
                85                  90                  95

Trp Trp Glu Gly Asp Leu Phe Gln Gly Lys Pro Asp Trp Lys Lys Leu
            100                 105                 110

His Asn Tyr Pro Gln Pro Arg Leu Thr Ala Glu Glu Gln Ala Phe Leu
        115                 120                 125

Asp Gly Pro Val Glu Glu Ala Cys Arg Met Ala Asn Asp Phe Gln Ile
    130                 135                 140

Thr His Glu Leu Ala Asp Leu Pro Pro Glu Leu Trp Ala Tyr Leu Lys
145                 150                 155                 160

Glu His Arg Phe Phe Ala Met Ile Ile Lys Lys Glu Tyr Gly Gly Leu
                165                 170                 175

Glu Phe Ser Ala Tyr Ala Gln Ser Arg Val Leu Gln Lys Leu Ser Gly
            180                 185                 190

Val Ser Gly Ile Leu Ala Ile Thr Val Gly Val Pro Asn Ser Leu Gly
        195                 200                 205
```

-continued

Pro Gly Glu Leu Leu Gln His Tyr Gly Thr Asp Gln Lys Asp His
    210                 215                 220

Tyr Leu Pro Arg Leu Ala Arg Gly Gln Glu Ile Pro Cys Phe Ala Leu
225                 230                 235                 240

Thr Ser Pro Glu Ala Gly Ser Asp Ala Gly Ala Ile Pro Asp Thr Gly
                245                 250                 255

Ile Val Cys Met Gly Glu Trp Gln Gly Gln Gln Val Leu Gly Met Arg
            260                 265                 270

Leu Thr Trp Asn Lys Arg Tyr Ile Thr Leu Ala Pro Ile Ala Thr Val
        275                 280                 285

Leu Gly Leu Ala Phe Lys Leu Ser Asp Pro Glu Lys Leu Leu Gly Gly
    290                 295                 300

Ala Glu Asp Leu Gly Ile Thr Cys Ala Leu Ile Pro Thr Thr Thr Pro
305                 310                 315                 320

Gly Val Glu Ile Gly Arg Arg His Phe Pro Leu Asn Val Pro Phe Gln
                325                 330                 335

Asn Gly Pro Thr Arg Gly Lys Asp Val Phe Val Pro Ile Asp Tyr Ile
            340                 345                 350

Ile Gly Gly Pro Lys Met Ala Gly Gln Gly Trp Arg Met Leu Val Glu
        355                 360                 365

Cys Leu Ser Val Gly Arg Gly Ile Thr Leu Pro Ser Asn Ser Thr Gly
    370                 375                 380

Gly Val Lys Ser Val Ala Leu Ala Thr Gly Ala Tyr Ala His Ile Arg
385                 390                 395                 400

Arg Gln Phe Lys Ile Ser Ile Gly Lys Met Glu Gly Ile Glu Glu Pro
                405                 410                 415

Leu Ala Arg Ile Ala Gly Asn Ala Tyr Val Met Asp Ala Ala Ala Ser
            420                 425                 430

Leu Ile Thr Tyr Gly Ile Met Leu Gly Glu Lys Pro Ala Val Leu Ser
        435                 440                 445

Ala Ile Val Lys Tyr His Cys Thr His Arg Gly Gln Gln Ser Ile Ile
    450                 455                 460

Asp Ala Met Asp Ile Thr Gly Gly Lys Gly Ile Met Leu Gly Gln Ser
465                 470                 475                 480

Asn Phe Leu Ala Arg Ala Tyr Gln Gly Ala Pro Ile Ala Ile Thr Val
                485                 490                 495

Glu Gly Ala Asn Ile Leu Thr Arg Ser Met Met Ile Phe Gly Gln Gly
            500                 505                 510

Ala Ile Arg Cys His Pro Tyr Val Leu Glu Glu Met Glu Ala Ala Lys
        515                 520                 525

Asn Asn Asp Val Asn Ala Phe Asp Lys Leu Leu Phe Lys His Ile Gly
    530                 535                 540

His Val Gly Ser Asn Lys Val Arg Ser Phe Trp Leu Gly Leu Thr Arg
545                 550                 555                 560

Gly Leu Thr Ser Ser Thr Pro Thr Gly Asp Ala Thr Lys Arg Tyr Tyr
                565                 570                 575

Gln His Leu Asn Arg Leu Ser Ala Asn Leu Ala Leu Leu Ser Asp Val
            580                 585                 590

Ser Met Ala Val Leu Gly Gly Ser Leu Lys Arg Arg Glu Arg Ile Ser
        595                 600                 605

Ala Arg Leu Gly Asp Ile Leu Ser Gln Leu Tyr Leu Ala Ser Ala Val
    610                 615                 620

-continued

```
Leu Lys Arg Tyr Asp Asp Glu Gly Arg Asn Glu Ala Asp Leu Pro Leu
625                 630                 635                 640

Val His Trp Gly Val Gln Asp Ala Leu Tyr Gln Ala Glu Gln Ala Met
            645                 650                 655

Asp Asp Leu Leu Gln Asn Phe Pro Asn Arg Val Val Ala Gly Leu Leu
        660                 665                 670

Asn Val Val Ile Phe Pro Thr Gly Arg His Tyr Leu Ala Pro Ser Asp
    675                 680                 685

Lys Leu Asp His Lys Val Ala Lys Ile Leu Gln Val Pro Asn Ala Thr
690                 695                 700

Arg Ser Arg Ile Gly Arg Gly Gln Tyr Leu Thr Pro Ser Glu His Asn
705                 710                 715                 720

Pro Val Gly Leu Leu Glu Glu Ala Leu Val Asp Val Ile Ala Ala Asp
            725                 730                 735

Pro Ile His Gln Arg Ile Cys Lys Glu Leu Gly Lys Asn Leu Pro Phe
        740                 745                 750

Thr Arg Leu Asp Glu Leu Ala His Asn Ala Leu Val Lys Gly Leu Ile
    755                 760                 765

Asp Lys Asp Glu Ala Ala Ile Leu Val Lys Ala Glu Glu Ser Arg Leu
770                 775                 780

Arg Ser Ile Asn Val Asp Asp Phe Asp Pro Glu Glu Leu Ala Thr Lys
785                 790                 795                 800

Pro Val Lys Leu Pro Glu Lys Val Arg Lys Val Glu Ala Ala
            805                 810

<210> SEQ ID NO 5
<211> LENGTH: 729
<212> TYPE: PRT
<213> ORGANISM: Escherichia coli

<400> SEQUENCE: 5

Met Leu Tyr Lys Gly Asp Thr Leu Tyr Leu Asp Trp Leu Glu Asp Gly
1               5                   10                  15

Ile Ala Glu Leu Val Phe Asp Ala Pro Gly Ser Val Asn Lys Leu Asp
            20                  25                  30

Thr Ala Thr Val Ala Ser Leu Gly Glu Ala Ile Gly Val Leu Glu Gln
        35                  40                  45

Gln Ser Asp Leu Lys Gly Leu Leu Leu Arg Ser Asn Lys Ala Ala Phe
    50                  55                  60

Ile Val Gly Ala Asp Ile Thr Glu Phe Leu Ser Leu Phe Leu Val Pro
65                  70                  75                  80

Glu Glu Gln Leu Ser Gln Trp Leu His Phe Ala Asn Ser Val Phe Asn
            85                  90                  95

Arg Leu Glu Asp Leu Pro Val Pro Thr Ile Ala Ala Val Asn Gly Tyr
        100                 105                 110

Ala Leu Gly Gly Gly Cys Glu Cys Val Leu Ala Thr Asp Tyr Arg Leu
    115                 120                 125

Ala Thr Pro Asp Leu Arg Ile Gly Leu Pro Glu Thr Lys Leu Gly Ile
130                 135                 140

Met Pro Gly Phe Gly Gly Ser Val Arg Met Pro Arg Met Leu Gly Ala
145                 150                 155                 160

Asp Ser Ala Leu Glu Ile Ile Ala Ala Gly Lys Asp Val Gly Ala Asp
            165                 170                 175

Gln Ala Leu Lys Ile Gly Leu Val Asp Gly Val Val Lys Ala Glu Lys
        180                 185                 190
```

```
Leu Val Glu Gly Ala Lys Ala Val Leu Arg Gln Ala Ile Asn Gly Asp
            195                 200                 205

Leu Asp Trp Lys Ala Lys Arg Gln Pro Lys Leu Glu Pro Leu Lys Leu
    210                 215                 220

Ser Lys Ile Glu Ala Thr Met Ser Phe Thr Ile Ala Lys Gly Met Val
225                 230                 235                 240

Ala Gln Thr Ala Gly Lys His Tyr Pro Ala Pro Ile Thr Ala Val Lys
                245                 250                 255

Thr Ile Glu Ala Ala Ala Arg Phe Gly Arg Glu Ala Leu Asn Leu
            260                 265                 270

Glu Asn Lys Ser Phe Val Pro Leu Ala His Thr Asn Glu Ala Arg Ala
            275                 280                 285

Leu Val Gly Ile Phe Leu Asn Asp Gln Tyr Val Lys Gly Lys Ala Lys
            290                 295                 300

Lys Leu Thr Lys Asp Val Glu Thr Pro Lys Gln Ala Ala Val Leu Gly
305                 310                 315                 320

Ala Gly Ile Met Gly Gly Gly Ile Ala Tyr Gln Ser Ala Trp Lys Gly
                325                 330                 335

Val Pro Val Met Lys Asp Ile Asn Asp Lys Ser Leu Thr Leu Gly
            340                 345                 350

Met Thr Glu Ala Ala Lys Leu Leu Asn Lys Gln Leu Glu Arg Gly Lys
            355                 360                 365

Ile Asp Gly Leu Lys Leu Ala Gly Val Ile Ser Thr Ile His Pro Thr
            370                 375                 380

Leu Asp Tyr Ala Gly Phe Asp Arg Val Asp Ile Val Val Glu Ala Val
385                 390                 395                 400

Val Glu Asn Pro Lys Val Lys Lys Ala Val Leu Ala Glu Thr Glu Gln
                405                 410                 415

Lys Val Arg Gln Asp Thr Val Leu Ala Ser Asn Thr Ser Thr Ile Pro
            420                 425                 430

Ile Ser Glu Leu Ala Asn Ala Leu Glu Arg Pro Glu Asn Phe Cys Gly
            435                 440                 445

Met His Phe Phe Asn Pro Val His Arg Met Pro Leu Val Glu Ile Ile
            450                 455                 460

Arg Gly Glu Lys Ser Ser Asp Glu Thr Ile Ala Lys Val Val Ala Trp
465                 470                 475                 480

Ala Ser Lys Met Gly Lys Thr Pro Ile Val Val Asn Asp Cys Pro Gly
                485                 490                 495

Phe Phe Val Asn Arg Val Leu Phe Pro Tyr Phe Ala Gly Phe Ser Gln
            500                 505                 510

Leu Leu Arg Asp Gly Ala Asp Phe Arg Lys Ile Asp Lys Val Met Glu
            515                 520                 525

Lys Gln Phe Gly Trp Pro Met Gly Pro Ala Tyr Leu Leu Asp Val Val
            530                 535                 540

Gly Ile Asp Thr Ala His His Ala Gln Ala Val Met Ala Ala Gly Phe
545                 550                 555                 560

Pro Gln Arg Met Gln Lys Asp Tyr Arg Asp Ala Ile Asp Ala Leu Phe
                565                 570                 575

Asp Ala Asn Arg Phe Gly Gln Lys Asn Gly Leu Gly Phe Trp Arg Tyr
            580                 585                 590

Lys Glu Asp Ser Lys Gly Lys Pro Lys Lys Glu Glu Asp Ala Ala Val
            595                 600                 605
```

```
Glu Asp Leu Leu Ala Glu Val Ser Gln Pro Lys Arg Asp Phe Ser Glu
610                 615                 620
Glu Glu Ile Ile Ala Arg Met Met Ile Pro Met Val Asn Glu Val Val
625                 630                 635                 640
Arg Cys Leu Glu Glu Gly Ile Ile Ala Thr Pro Ala Glu Ala Asp Met
            645                 650                 655
Ala Leu Val Tyr Gly Leu Gly Phe Pro Phe His Gly Gly Ala Phe
        660                 665                 670
Arg Trp Leu Asp Thr Leu Gly Ser Ala Lys Tyr Leu Asp Met Ala Gln
            675                 680                 685
Gln Tyr Gln His Leu Gly Pro Leu Tyr Glu Val Pro Glu Gly Leu Arg
        690                 695                 700
Asn Lys Ala Arg His Asn Glu Pro Tyr Tyr Pro Val Glu Pro Ala
705                 710                 715                 720
Arg Pro Val Gly Asp Leu Lys Thr Ala
                725

<210> SEQ ID NO 6
<211> LENGTH: 387
<212> TYPE: PRT
<213> ORGANISM: Escherichia coli

<400> SEQUENCE: 6

Met Glu Gln Val Val Ile Val Asp Ala Ile Arg Thr Pro Met Gly Arg
1               5                   10                  15
Ser Lys Gly Gly Ala Phe Arg Asn Val Arg Ala Glu Asp Leu Ser Ala
            20                  25                  30
His Leu Met Arg Ser Leu Leu Ala Arg Asn Pro Ala Leu Glu Ala Ala
        35                  40                  45
Ala Leu Asp Asp Ile Tyr Trp Gly Cys Val Gln Gln Thr Leu Glu Gln
    50                  55                  60
Gly Phe Asn Ile Ala Arg Asn Ala Ala Leu Leu Ala Glu Val Pro His
65                  70                  75                  80
Ser Val Pro Ala Val Thr Val Asn Arg Leu Cys Gly Ser Ser Met Gln
                85                  90                  95
Ala Leu His Asp Ala Ala Arg Met Ile Met Thr Gly Asp Ala Gln Ala
            100                 105                 110
Cys Leu Val Gly Gly Val Glu His Met Gly His Val Pro Met Ser His
        115                 120                 125
Gly Val Asp Phe His Pro Gly Leu Ser Arg Asn Val Ala Lys Ala Ala
    130                 135                 140
Gly Met Met Gly Leu Thr Ala Glu Met Leu Ala Arg Met His Gly Ile
145                 150                 155                 160
Ser Arg Glu Met Gln Asp Ala Phe Ala Ala Arg Ser His Ala Arg Ala
                165                 170                 175
Trp Ala Ala Thr Gln Ser Ala Ala Phe Lys Asn Glu Ile Ile Pro Thr
            180                 185                 190
Gly Gly His Asp Ala Asp Gly Val Leu Lys Gln Phe Asn Tyr Asp Glu
        195                 200                 205
Val Ile Arg Pro Glu Thr Thr Val Glu Ala Leu Ala Thr Leu Arg Pro
    210                 215                 220
Ala Phe Asp Pro Val Asn Gly Met Val Thr Ala Gly Thr Ser Ser Ala
225                 230                 235                 240
Leu Ser Asp Gly Ala Ala Ala Met Leu Val Met Ser Glu Ser Arg Ala
                245                 250                 255
```

His Glu Leu Gly Leu Lys Pro Arg Ala Arg Val Arg Ser Met Ala Val
            260                 265                 270

Val Gly Cys Asp Pro Ser Ile Met Gly Tyr Gly Pro Val Pro Ala Ser
            275                 280                 285

Lys Leu Ala Leu Lys Ala Gly Leu Ser Ala Ser Asp Ile Gly Val
            290                 295                 300

Phe Glu Met Asn Glu Ala Phe Ala Ala Gln Ile Leu Pro Cys Ile Lys
305                 310                 315                 320

Asp Leu Gly Leu Ile Glu Gln Ile Asp Glu Lys Ile Asn Leu Asn Gly
                325                 330                 335

Gly Ala Ile Ala Leu Gly His Pro Leu Gly Cys Ser Gly Ala Arg Ile
            340                 345                 350

Ser Thr Thr Leu Leu Asn Leu Met Glu Arg Lys Asp Val Gln Phe Gly
            355                 360                 365

Leu Ala Thr Met Cys Ile Gly Leu Gly Gln Gly Ile Ala Thr Val Phe
            370                 375                 380

Glu Arg Val
385

<210> SEQ ID NO 7
<211> LENGTH: 339
<212> TYPE: PRT
<213> ORGANISM: Bacillus stearothermophilus

<400> SEQUENCE: 7

Met Lys Ala Ala Val Val Glu Gln Phe Lys Glu Pro Leu Lys Ile Lys
1               5                   10                  15

Glu Val Glu Lys Pro Thr Ile Ser Tyr Gly Glu Val Leu Val Arg Ile
            20                  25                  30

Lys Ala Cys Gly Val Cys His Thr Asp Leu His Ala Ala His Gly Asp
            35                  40                  45

Trp Pro Val Lys Pro Lys Leu Pro Leu Ile Pro Gly His Glu Gly Val
    50                  55                  60

Gly Ile Val Glu Glu Val Gly Pro Gly Val Thr His Leu Lys Val Gly
65                  70                  75                  80

Asp Arg Val Gly Ile Pro Trp Leu Tyr Ser Ala Cys Gly His Cys Asp
                85                  90                  95

Tyr Cys Leu Ser Gly Gln Glu Thr Leu Cys Glu His Gln Lys Asn Ala
            100                 105                 110

Gly Tyr Ser Val Asp Gly Gly Tyr Ala Glu Tyr Cys Arg Ala Ala Ala
            115                 120                 125

Asp Tyr Val Val Lys Ile Pro Asp Asn Leu Ser Phe Glu Glu Ala Ala
            130                 135                 140

Pro Ile Phe Cys Ala Gly Val Thr Thr Tyr Lys Ala Leu Lys Val Thr
145                 150                 155                 160

Gly Ala Lys Pro Gly Glu Trp Val Ala Ile Tyr Gly Ile Gly Gly Leu
            165                 170                 175

Gly His Val Ala Val Gln Tyr Ala Lys Ala Met Gly Leu Asn Val Val
            180                 185                 190

Ala Val Asp Ile Gly Asp Glu Lys Leu Glu Leu Ala Lys Glu Leu Gly
            195                 200                 205

Ala Asp Leu Val Val Asn Pro Leu Lys Glu Asp Ala Ala Lys Phe Met
            210                 215                 220

Lys Glu Lys Val Gly Gly Val His Ala Ala Val Val Thr Ala Val Ser

Lys Pro Ala Phe Gln Ser Ala Tyr Asn Ser Ile Arg Arg Gly Gly Ala
225                 230                 235                 240

Cys Val Leu Val Gly Leu Pro Pro Glu Glu Met Pro Ile Pro Ile Phe
            245                 250                 255

Asp Thr Val Leu Asn Gly Ile Lys Ile Ile Gly Ser Ile Val Gly Thr
        260                 265                 270

Arg Lys Asp Leu Gln Glu Ala Leu Gln Phe Ala Ala Glu Gly Lys Val
    275                 280                 285

Lys Thr Ile Ile Glu Val Gln Pro Leu Glu Lys Ile Asn Glu Val Phe
290                 295                 300

Asp Arg Met Leu Lys Gly Gln Ile Asn Gly Arg Val Val Leu Thr Leu
305                 310                 315                 320

Glu Asp Lys
                325                 330                 335

<210> SEQ ID NO 8
<211> LENGTH: 346
<212> TYPE: PRT
<213> ORGANISM: Rhodococcus ruber

<400> SEQUENCE: 8

Met Lys Ala Leu Gln Tyr Thr Glu Ile Gly Ser Glu Pro Val Val Val
1               5                   10                  15

Asp Val Pro Thr Pro Ala Pro Gly Pro Gly Glu Ile Leu Leu Lys Val
            20                  25                  30

Thr Ala Ala Gly Leu Cys His Ser Asp Ile Phe Val Met Asp Met Pro
        35                  40                  45

Ala Glu Gln Tyr Ile Tyr Gly Leu Pro Leu Thr Leu Gly His Glu Gly
    50                  55                  60

Val Gly Thr Val Ala Glu Leu Gly Ala Gly Val Thr Gly Phe Glu Thr
65                  70                  75                  80

Gly Asp Ala Val Ala Val Tyr Gly Pro Trp Gly Cys Gly Ala Cys His
                85                  90                  95

Ala Cys Ala Arg Gly Arg Glu Asn Tyr Cys Thr Arg Ala Ala Glu Leu
            100                 105                 110

Gly Ile Thr Pro Pro Gly Leu Gly Ser Pro Gly Ser Met Ala Glu Tyr
        115                 120                 125

Met Ile Val Asp Ser Ala Arg His Leu Val Pro Ile Gly Asp Leu Asp
    130                 135                 140

Pro Val Ala Ala Val Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175

Val Ile Gly Val Gly Gly Leu Gly His Val Gly Ile Gln Ile Leu Arg
            180                 185                 190

Ala Val Ser Ala Ala Arg Val Ile Ala Val Asp Leu Asp Asp Asp Arg
        195                 200                 205

Leu Ala Leu Ala Arg Glu Val Gly Ala Asp Ala Val Lys Ser Gly
    210                 215                 220

Ala Gly Ala Ala Asp Ala Ile Arg Glu Leu Thr Gly Gly Glu Gly Ala
225                 230                 235                 240

Thr Ala Val Phe Asp Phe Val Gly Ala Gln Ser Thr Ile Asp Thr Ala
                245                 250                 255

Gln Gln Val Val Ala Ile Asp Gly His Ile Ser Val Val Gly Ile His

```
            260                 265                 270
Ala Gly Ala His Ala Lys Val Gly Phe Phe Met Ile Pro Phe Gly Ala
            275                 280                 285

Ser Val Val Thr Pro Tyr Trp Gly Thr Arg Ser Glu Leu Met Asp Val
            290                 295                 300

Val Asp Leu Ala Arg Ala Gly Arg Leu Asp Ile His Thr Glu Thr Phe
305                 310                 315                 320

Thr Leu Asp Glu Gly Pro Thr Ala Tyr Arg Arg Leu Arg Glu Gly Ser
                325                 330                 335

Ile Arg Gly Arg Gly Val Val Val Pro Gly
                340                 345

<210> SEQ ID NO 9
<211> LENGTH: 249
<212> TYPE: PRT
<213> ORGANISM: Ralstonia eutropha

<400> SEQUENCE: 9

Met Tyr Arg Leu Leu Asn Lys Thr Ala Val Ile Thr Gly Gly Asn Ser
1               5                   10                  15

Gly Ile Gly Leu Ala Thr Ala Lys Arg Phe Val Ala Glu Gly Ala Tyr
            20                  25                  30

Val Phe Ile Val Gly Arg Arg Lys Glu Leu Glu Gln Ala Ala Ala
        35                  40                  45

Glu Ile Gly Arg Asn Val Thr Ala Val Lys Ala Asp Val Thr Lys Leu
    50                  55                  60

Glu Asp Leu Asp Arg Leu Tyr Ala Ile Val Arg Glu Gln Arg Gly Ser
65                  70                  75                  80

Ile Asp Val Leu Phe Ala Asn Ser Gly Ala Ile Glu Gln Lys Thr Leu
                85                  90                  95

Glu Glu Ile Thr Pro Glu His Tyr Asp Arg Thr Phe Asp Val Asn Val
            100                 105                 110

Arg Gly Leu Ile Phe Thr Val Gln Lys Ala Leu Pro Leu Leu Arg Asp
        115                 120                 125

Gly Gly Ser Val Ile Leu Thr Ser Ser Val Ala Gly Val Leu Gly Leu
    130                 135                 140

Gln Ala His Asp Thr Tyr Ser Ala Ala Lys Ala Ala Val Arg Ser Leu
145                 150                 155                 160

Ala Arg Thr Trp Thr Thr Glu Leu Lys Gly Arg Ser Ile Arg Val Asn
                165                 170                 175

Ala Val Ser Pro Gly Ala Ile Asp Thr Pro Ile Ile Glu Asn Gln Val
            180                 185                 190

Ser Thr Gln Glu Glu Ala Asp Glu Leu Arg Ala Lys Phe Ala Ala Ala
        195                 200                 205

Thr Pro Leu Gly Arg Val Gly Arg Pro Glu Glu Leu Ala Ala Ala Val
    210                 215                 220

Leu Phe Leu Ala Ser Asp Asp Ser Ser Tyr Val Ala Gly Ile Glu Leu
225                 230                 235                 240

Phe Val Asp Gly Gly Leu Thr Gln Val
                245

<210> SEQ ID NO 10
<211> LENGTH: 338
<212> TYPE: PRT
<213> ORGANISM: Lactobacillus brevis
```

<400> SEQUENCE: 10

Met Lys Ala Ala Val Ile Arg Asp Ser Val Asp Gly Tyr Val Asp Ile
1               5                   10                  15

Lys Asp Val Thr Leu Arg Pro Ile Thr His Gly Glu Ala Leu Val Lys
            20                  25                  30

Met Glu Tyr Cys Gly Leu Cys His Thr Asp Leu His Val Ala Ala Gly
        35                  40                  45

Asp Phe Gly Lys Gln Pro Gly Arg Ile Ile Gly His Glu Gly Val Gly
    50                  55                  60

Lys Val Ile Gln Val Ala Asp Asp Val Asp Asn Leu Lys Ile Gly Asp
65                  70                  75                  80

Arg Val Ser Val Ala Trp Phe Phe Lys Gly Cys Gly His Cys Glu Tyr
                85                  90                  95

Cys Leu Thr Gly Arg Glu Thr Leu Cys Arg Asn Val Gln Asn Ser Gly
            100                 105                 110

Phe Thr Val Asp Gly Ala Met Ala Glu Glu Cys Ile Val Asp Ala Asn
        115                 120                 125

Tyr Ala Val Lys Val Pro Glu Gly Leu Asp Pro Ile Glu Ala Thr Ser
    130                 135                 140

Leu Thr Cys Ala Gly Val Thr Met Tyr Lys Ala Leu Lys Val Gly Glu
145                 150                 155                 160

Thr Lys Pro Gly Gln Trp Val Glu Val Gly Ala Gly Gly Leu Gly
                165                 170                 175

Asn Leu Ala Ile Gln Tyr Ala His Asn Val Phe Gly Ala His Val Val
            180                 185                 190

Ala Val Asp Gly Asn Pro Asp Lys Leu Ala Ala Ala Lys Ala Asn Gly
        195                 200                 205

Ala Glu Val Leu Ile Asn Arg His Asp Gly Asn Val Ala Glu Gln Ile
    210                 215                 220

Gln Glu Lys Val Gly Gly Val Asp Asn Ala Gln Val Thr Ala Val Asn
225                 230                 235                 240

Lys Asp Ala Phe Thr Gln Ser Val Asn Ala Leu Lys Pro Asp Gly Lys
                245                 250                 255

Leu Val Ala Val Ala Leu Pro Gln Gly Asp Met Glu Leu Asn Ile Ala
            260                 265                 270

Lys Thr Val Leu Asp Gly Ile Ser Val Arg Gly Ser Leu Val Gly Thr
        275                 280                 285

Arg Gln Asp Leu Ala Glu Thr Phe Gln Phe Gly Ala Glu Gly Lys Val
    290                 295                 300

His Pro Ile Val Lys Thr Arg Arg Leu Asp Glu Val Asn Asp Ile Ile
305                 310                 315                 320

Asp Glu Met Lys Asn Asn Gln Ile Val Gly Arg Met Val Val Asp Phe
                325                 330                 335

Thr Lys

<210> SEQ ID NO 11
<211> LENGTH: 347
<212> TYPE: PRT
<213> ORGANISM: Lactobacillus kefir

<400> SEQUENCE: 11

Met Lys Ser Thr Ile Phe Val Lys Pro Gly Lys Val Glu Ile Gln Asn
1               5                   10                  15

Ile Asp Lys Pro Thr Ile Gln Ala Asp Asp Ala Ile Leu His Ile

```
            20                  25                  30
Val Arg Ala Cys Val Cys Gly Ser Asp Leu Trp Ala Tyr Arg Asp Leu
        35                  40                  45
Glu Asp Lys Glu Pro Asn Ser Glu Asn Thr Gly His Glu Ala Ile Ala
50                  55                  60
Ile Val Asp Gln Val Gly Lys Asn Ile Thr Thr Val Lys Pro Gly Asp
65                  70                  75                  80
Phe Val Ile Ala Pro Phe Thr His Gly Cys Gly His Cys Ala Ala Cys
                85                  90                  95
Arg Ala Gly Tyr Glu Gly Ser Cys Gln Ser His Ser Asp Asn Phe Ser
            100                 105                 110
Ala Gly Tyr Gln Ala Glu Tyr Val Arg Tyr Gln His Ala Glu Trp Ser
            115                 120                 125
Leu Val Lys Ile Pro Gly Lys Pro Glu Asp Tyr Ser Asp Gly Met Leu
            130                 135                 140
Asn Ser Leu Leu Thr Leu Ala Asp Val Met Ala Thr Gly Tyr His Ala
145                 150                 155                 160
Ala Arg Val Ala Asn Val Lys Pro Gly Asp Thr Val Val Val Gly
                165                 170                 175
Asp Gly Ala Val Gly Leu Cys Gly Val Ile Ala Ser Gln Met Arg Gly
            180                 185                 190
Ala Ser Arg Ile Ile Ala Met Ser Arg His Glu Asp Arg Gln Lys Leu
            195                 200                 205
Ala Thr Glu Phe Gly Ala Thr Asp Ile Val Pro Glu Arg Gly Asp Glu
            210                 215                 220
Ala Val Ala Lys Val Met Ala Leu Thr Asn Gly Ala Gly Ala Asp Ala
225                 230                 235                 240
Val Leu Glu Cys Val Gly Ser Glu Leu Ser Thr Asp Thr Ala Met Lys
                245                 250                 255
Val Ala Arg Pro Gly Ala Thr Val Gly Arg Val Gly Leu Pro His Thr
            260                 265                 270
Lys Lys Thr Asp Leu Thr Asn Ser Phe Tyr Ser Asn Leu Ala Ile Ala
            275                 280                 285
Gly Gly Pro Ala Ser Val Thr Thr Tyr Asp Lys Ser Val Leu Leu Lys
            290                 295                 300
Ala Val Leu Asp Gly Asp Ile His Pro Gly Lys Val Phe Thr Lys Arg
305                 310                 315                 320
Phe Thr Leu Asp Glu Ile Asp Asp Ala Tyr Gln Ala Met Ala Lys Arg
                325                 330                 335
Glu Ala Ile Lys Ser Leu Val Val Ala Gln Lys
            340                 345

<210> SEQ ID NO 12
<211> LENGTH: 262
<212> TYPE: PRT
<213> ORGANISM: Paracoccus pantotrophus

<400> SEQUENCE: 12

Met Ser Asn Ser Val Glu Gly Arg Val Val Ile Val Thr Gly Ala Gly
1               5                   10                  15
Arg Gly Ile Gly Arg Ser Ile Ala Glu Gly Leu Ala Gln Ala Gly Ala
            20                  25                  30
Arg Val Val Ile Ala Asp Ile Ala Ala Asp Thr Ala Glu Thr Thr Ala
        35                  40                  45
```

Ala Glu Ile Arg Glu Ala Gly Gly Gln Ala Ile Gly Leu Ala Val Asp
 50                  55                  60

Val Thr Asp Arg Ala Ser Thr Arg Ala Leu Ile Ala Arg Thr Val Ala
 65                  70                  75                  80

Glu His Gly Arg Leu Asp Ala Met Phe Asn Asn Ala Gly Ile Ala Gln
                 85                  90                  95

Val Lys Pro Phe Asn Asp Ile Thr Glu Asp Asp Trp His Arg Val Met
            100                 105                 110

Asp Val Asn Ala Met Gly Val Leu Ile Gly Ile Gln Glu Ala Ala Arg
        115                 120                 125

Gln Phe Ile Ala Gln Gly Gly Gly Lys Ile Val Asn Thr Ala Ser
130                 135                 140

Ile Ala Gly Lys Gln Gly Tyr Glu Pro Leu Ala His Tyr Ser Ala Ser
145                 150                 155                 160

Lys Phe Ala Val Val Ala Leu Thr Gln Ala Ala Arg Ala Phe Gly
                165                 170                 175

Lys His Gly Ile Cys Val Asn Ala Ile Cys Pro Gly Val Val Ala Thr
            180                 185                 190

Asp Met Trp Lys Leu Ile Asp Lys Gly Phe Lys Asp Glu Gly Leu Thr
        195                 200                 205

Ser Arg Asp Asn Glu Ala Phe Glu Gly Phe Ser Ala Asp Ile Leu Leu
210                 215                 220

Gly Arg Pro Ser Arg Pro Glu Asp Leu Ala Gly Val Ser Ile Phe Leu
225                 230                 235                 240

Ala Ser Ala Gly Ser Asp Tyr Met Thr Gly Gln Ser Leu Val Val Asp
                245                 250                 255

Gly Gly Met Val Leu Leu
            260

<210> SEQ ID NO 13
<211> LENGTH: 262
<212> TYPE: PRT
<213> ORGANISM: Sphingobium yanoikuyae

<400> SEQUENCE: 13

Met Thr Thr Leu Pro Thr Val Leu Ile Thr Gly Ala Ser Ser Gly Ile
1               5                   10                  15

Gly Ala Thr Tyr Ala Glu Arg Phe Ala Arg Arg Gly His Asp Leu Val
                20                  25                  30

Leu Val Ala Arg Asp Lys Val Arg Leu Asp Ala Leu Ala Ala Arg Leu
            35                  40                  45

Arg Asp Glu Ser Gly Val Ala Val Glu Ala Leu Gln Ala Asp Leu Thr
 50                  55                  60

Arg Pro Ala Asp Leu Ala Val Glu Ile Leu Arg Glu Asp Ala
 65                  70                  75                  80

Arg Ile Gly Ile Leu Ile Asn Asn Ala Gly Met Ala Gln Ser Gly Gly
                 85                  90                  95

Phe Val Gln Gln Thr Ala Glu Gly Ile Glu Arg Leu Ile Thr Leu Asn
            100                 105                 110

Thr Thr Ala Leu Thr Arg Leu Ala Ala Ala Val Ala Pro Arg Phe Val
        115                 120                 125

Gln Ser Gly Thr Gly Ala Ile Val Asn Ile Gly Ser Val Val Gly Phe
130                 135                 140

Ala Pro Glu Phe Gly Met Ser Ile Tyr Gly Ala Thr Lys Ala Phe Val
145                 150                 155                 160

```
Leu Phe Leu Ser Gln Gly Leu Asn Leu Glu Leu Ser Pro Ser Gly Ile
                165                 170                 175

Tyr Val Gln Ala Val Leu Pro Ala Ala Thr Arg Thr Glu Ile Trp Gly
            180                 185                 190

Arg Ala Gly Ile Asp Val Asn Thr Leu Pro Glu Val Met Glu Val Asp
        195                 200                 205

Glu Leu Val Asp Ala Ala Leu Val Gly Phe Asp Arg Arg Glu Leu Val
    210                 215                 220

Thr Ile Pro Pro Leu His Val Ala Ala Arg Trp Asp Ala Leu Asp Gly
225                 230                 235                 240

Ala Arg Gln Gly Leu Met Ser Asp Ile Arg Gln Ala Gln Ala Ala Asp
                245                 250                 255

Arg Tyr Arg Pro Glu Ala
                260

<210> SEQ ID NO 14
<211> LENGTH: 459
<212> TYPE: PRT
<213> ORGANISM: Chromobacterium violaceum

<400> SEQUENCE: 14

Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Ser Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
```

```
                    260                 265                 270
Gly His Gln His Phe Gly Phe Gln Pro Asp Leu Phe Thr Ala Ala Lys
            275                 280                 285
Gly Leu Ser Ser Gly Tyr Leu Pro Ile Gly Ala Val Phe Val Gly Lys
            290                 295                 300
Arg Val Ala Glu Gly Leu Ile Ala Gly Gly Asp Phe Asn His Gly Phe
305                 310                 315                 320
Thr Tyr Ser Gly His Pro Val Cys Ala Ala Val Ala His Ala Asn Val
                325                 330                 335
Ala Ala Leu Arg Asp Glu Gly Ile Val Gln Arg Val Lys Asp Asp Ile
            340                 345                 350
Gly Pro Tyr Met Gln Lys Arg Trp Arg Glu Thr Phe Ser Arg Phe Glu
            355                 360                 365
His Val Asp Asp Val Arg Gly Val Gly Met Val Gln Ala Phe Thr Leu
        370                 375                 380
Val Lys Asn Lys Ala Lys Arg Glu Leu Phe Pro Asp Phe Gly Glu Ile
385                 390                 395                 400
Gly Thr Leu Cys Arg Asp Ile Phe Phe Arg Asn Asn Leu Ile Met Arg
                405                 410                 415
Ala Cys Gly Asp His Ile Val Ser Ala Pro Pro Leu Val Met Thr Arg
            420                 425                 430
Ala Glu Val Asp Glu Met Leu Ala Val Ala Glu Arg Cys Leu Glu Glu
            435                 440                 445
Phe Glu Gln Thr Leu Lys Ala Arg Gly Leu Ala
    450                 455

<210> SEQ ID NO 15
<211> LENGTH: 378
<212> TYPE: PRT
<213> ORGANISM: Bacillus subtilis

<400> SEQUENCE: 15

Met Ile Ile Gly Val Pro Lys Glu Ile Lys Asn Asn Glu Asn Arg Val
1               5                   10                  15
Ala Leu Thr Pro Gly Gly Val Ser Gln Leu Ile Ser Asn Gly His Arg
            20                  25                  30
Val Leu Val Glu Thr Gly Ala Gly Leu Gly Ser Gly Phe Glu Asn Glu
        35                  40                  45
Ala Tyr Glu Ser Ala Gly Ala Glu Ile Ile Ala Asp Pro Lys Gln Val
    50                  55                  60
Trp Asp Ala Glu Met Val Met Lys Val Lys Glu Pro Leu Pro Glu Glu
65                  70                  75                  80
Tyr Val Tyr Phe Arg Lys Gly Leu Val Leu Phe Thr Tyr Leu His Leu
                85                  90                  95
Ala Ala Glu Pro Glu Leu Ala Gln Ala Leu Lys Asp Lys Gly Val Thr
            100                 105                 110
Ala Ile Ala Tyr Glu Thr Val Ser Glu Gly Arg Thr Leu Pro Leu Leu
        115                 120                 125
Thr Pro Met Ser Glu Val Ala Gly Arg Met Ala Ala Gln Ile Gly Ala
    130                 135                 140
Gln Phe Leu Glu Lys Pro Lys Gly Gly Lys Gly Ile Leu Leu Ala Gly
145                 150                 155                 160
Val Pro Gly Val Ser Arg Gly Lys Val Thr Ile Ile Gly Gly Gly Val
                165                 170                 175
```

```
Val Gly Thr Asn Ala Ala Lys Met Ala Val Gly Leu Gly Ala Asp Val
            180                 185                 190

Thr Ile Ile Asp Leu Asn Ala Asp Arg Leu Arg Gln Leu Asp Asp Ile
        195                 200                 205

Phe Gly His Gln Ile Lys Thr Leu Ile Ser Asn Pro Val Asn Ile Ala
        210                 215                 220

Asp Ala Val Ala Glu Ala Asp Leu Leu Ile Cys Ala Val Leu Ile Pro
225                 230                 235                 240

Gly Ala Lys Ala Pro Thr Leu Val Thr Glu Glu Met Val Lys Gln Met
                245                 250                 255

Lys Pro Gly Ser Val Ile Val Asp Val Ala Ile Asp Gln Gly Gly Ile
            260                 265                 270

Val Glu Thr Val Asp His Ile Thr Thr His Asp Gln Pro Thr Tyr Glu
        275                 280                 285

Lys His Gly Val Val His Tyr Ala Val Ala Asn Met Pro Gly Ala Val
        290                 295                 300

Pro Arg Thr Ser Thr Ile Ala Leu Thr Asn Val Thr Val Pro Tyr Ala
305                 310                 315                 320

Leu Gln Ile Ala Asn Lys Gly Ala Val Lys Ala Leu Ala Asp Asn Thr
                325                 330                 335

Ala Leu Arg Ala Gly Leu Asn Thr Ala Asn Gly His Val Thr Tyr Glu
            340                 345                 350

Ala Val Ala Arg Asp Leu Gly Tyr Glu Tyr Val Pro Ala Glu Lys Ala
        355                 360                 365

Leu Gln Asp Glu Ser Ser Val Ala Gly Ala
        370                 375

<210> SEQ ID NO 16
<211> LENGTH: 416
<212> TYPE: PRT
<213> ORGANISM: Rhizobium leguminosarum

<400> SEQUENCE: 16

Met Ala Asp Glu Thr Lys Lys Thr Val Ala Val Val Gly Ala Gly Val
1               5                   10                  15

Ile Gly Ala Ser Ile Ala Phe Glu Leu Gln Arg Arg Gly Phe Asp Val
            20                  25                  30

Thr Leu Ile Asp Lys Gly Glu Pro Gly Arg Gly Thr Ser Phe Gly Asn
        35                  40                  45

Met Ala Ser Ile Ala Leu Asp Phe Ala Ala Gly Ser Gly Pro Ser Thr
    50                  55                  60

Trp Lys Lys Ile Pro Gly Trp Leu Leu Asp Pro Glu Gly Pro Val Trp
65                  70                  75                  80

Leu Arg Pro Ser Tyr Ala Ala Arg Met Leu Pro Trp Phe Leu Arg Phe
                85                  90                  95

Leu Ala Ala Gly Arg Pro Ser Arg Leu Arg Glu Ile Glu Asp Ala Gly
            100                 105                 110

Met Arg Leu Ser Asn Arg Ala Leu Gly Asp Phe Arg Gln Met Leu Gln
        115                 120                 125

Ala Ile Gly Ala Pro Glu Leu Met Thr Glu Gly Cys Leu Ala Ile
    130                 135                 140

Tyr Glu Thr Glu Ala Glu Phe Ala Ala Asp Arg Gly His Leu Ala Met
145                 150                 155                 160

Met Gln Arg Tyr Gly Leu Glu Phe Glu Val Leu Ser Asn Gly Ala Ile
                165                 170                 175
```

```
Gln His Tyr Glu Pro Thr Leu Ser Pro Ala Ile Ala Lys Ala Val Leu
                180                 185                 190

Leu Pro Asp Asn Lys Ser Ile Arg Asp Pro Tyr Lys Leu Val Val Lys
            195                 200                 205

Leu Ala Asp Ala Ala Lys Ala Ala Gly Thr Thr Phe Val Ser Gly Thr
210                 215                 220

Val Arg Asn Ile Glu Arg Arg Gly Asp Gly Thr Ala Val Val Leu Leu
225                 230                 235                 240

Glu Asp Gly Arg Arg Ile Glu Ala Gly Ser Val Leu Ala Ala Gly
                245                 250                 255

Val His Thr Arg Phe Leu Ala Glu Lys Leu Gly Glu Pro Ile Pro Leu
                260                 265                 270

Glu Thr Glu Arg Gly Tyr His Thr Gln Ile Met Lys Pro Gly Ile Ala
            275                 280                 285

Met Arg Tyr Ser Val Ile Trp Pro His Arg Ala Phe Met Val Thr Pro
290                 295                 300

Thr Ala Gly Gly Ile Arg Val Gly Gly Asn Val Glu Leu Ala Gly Leu
305                 310                 315                 320

Asp Ala Ala Pro Asp Phe Arg Arg Pro Arg Val Leu Val Arg His Ala
                325                 330                 335

Gln Arg Ala Leu Pro Gly Leu Lys Val Glu Glu Thr Thr Glu Trp Met
                340                 345                 350

Gly His Arg Pro Ala Leu Pro Asp Thr Ile Pro Ile Ser Pro Ser
            355                 360                 365

Ser Lys Leu Pro Gly Val Phe Tyr Ala Thr Gly His Gly His Leu Gly
            370                 375                 380

Leu Thr Phe Ser Ala Thr Thr Ala Leu Val Ile Ala Asp Met Val Thr
385                 390                 395                 400

Gly Leu Lys Pro Ser Leu Asp Met Thr Pro Phe Arg Ile Asp Arg Tyr
                405                 410                 415

<210> SEQ ID NO 17
<211> LENGTH: 374
<212> TYPE: PRT
<213> ORGANISM: Vibrio proteolyticus

<400> SEQUENCE: 17

Met Ile Ile Gly Val Pro Lys Glu Ile Lys Asn His Glu Tyr Arg Val
1               5                   10                  15

Gly Met Ile Pro Ala Ser Val Arg Glu Leu Ile Ser His Gly His Gln
                20                  25                  30

Val Phe Val Glu Thr Asn Ala Gly Ala Gly Ile Gly Phe Ser Asp Asp
            35                  40                  45

Asp Tyr Ile Ala Val Gly Ala Ser Ile Leu Pro Thr Ala Ala Glu Val
    50                  55                  60

Phe Ala Gln Ala Asp Met Ile Val Lys Val Lys Glu Pro Gln Ala Val
65                  70                  75                  80

Glu Arg Ala Met Leu Lys Glu Gly Gln Ile Leu Phe Thr Tyr Leu His
                85                  90                  95

Leu Ala Pro Asp Phe Pro Gln Thr Glu Asp Leu Ile Lys Ser Lys Ala
            100                 105                 110

Val Cys Ile Ala Tyr Glu Thr Val Thr Asp Asn Met Gly Arg Leu Pro
        115                 120                 125

Leu Leu Ala Pro Met Ser Glu Val Ala Gly Arg Met Ser Ile Gln Ala
```

```
            130                 135                 140
Gly Ala Gln Thr Leu Glu Lys Ser His Gly Gly Arg Gly Leu Leu Leu
145                 150                 155                 160

Gly Gly Val Pro Gly Val Glu Pro Ala Lys Val Val Ile Val Gly Gly
                165                 170                 175

Gly Val Val Gly Ala Asn Ala Ala Arg Met Ala Val Gly Met Arg Ala
            180                 185                 190

Asp Val Thr Ile Leu Asp Arg Asn Ile Asp Thr Leu Arg Lys Leu Asp
        195                 200                 205

Glu Glu Phe Gln Gly Arg Ala Lys Val Val Tyr Ser Thr Glu Asp Ala
        210                 215                 220

Ile Glu Lys His Val Leu Ala Ala Asp Leu Val Ile Gly Ala Val Leu
225                 230                 235                 240

Ile Pro Gly Ala Ala Pro Lys Leu Val Thr Lys Glu His Ile Ala
                245                 250                 255

Lys Met Lys Pro Gly Ala Ala Val Val Asp Val Ala Ile Asp Gln Gly
                260                 265                 270

Gly Cys Phe Glu Thr Ser His Ala Thr Thr His Ala Asp Pro Thr Tyr
            275                 280                 285

Ile Val Asp Asp Val Val His Tyr Cys Val Ala Asn Met Pro Gly Ala
        290                 295                 300

Val Ala Arg Thr Ser Thr Phe Ala Leu Asn Asn Ala Thr Leu Pro Tyr
305                 310                 315                 320

Ile Val Lys Leu Ala Asn Lys Gly Tyr Arg Glu Ala Leu Leu Ala Asp
                325                 330                 335

His Gly Phe Leu Glu Gly Leu Asn Val Ile His Gly Lys Val Thr Cys
            340                 345                 350

Lys Glu Val Ala Glu Ala Phe Asn Leu Glu Tyr Val Gln Pro Glu Thr
        355                 360                 365

Ala Ile Ala Met Phe Asn
    370

<210> SEQ ID NO 18
<211> LENGTH: 373
<212> TYPE: PRT
<213> ORGANISM: Mycobacterium tuberculosis

<400> SEQUENCE: 18

Met Arg Val Gly Ile Pro Thr Glu Thr Lys Asn Asn Glu Phe Gln Phe
1               5                   10                  15

Arg Val Ala Ile Thr Pro Ala Gly Val Ala Glu Leu Thr Arg Arg Gly
            20                  25                  30

His Glu Val Leu Ile Gln Ala Gly Ala Gly Glu Gly Ser Ala Ile Thr
        35                  40                  45

Asp Ala Asp Phe Lys Ala Ala Gly Ala Gln Leu Val Gly Thr Ala Asp
    50                  55                  60

Gln Val Trp Ala Asp Ala Asp Leu Leu Leu Lys Val Lys Glu Pro Ile
65                  70                  75                  80

Ala Ala Glu Tyr Gly Arg Leu Arg His Gly Gln Ile Leu Phe Thr Phe
                85                  90                  95

Leu His Leu Ala Ala Ser Arg Ala Cys Thr Asp Ala Leu Leu Asp Ser
            100                 105                 110

Gly Thr Thr Ser Ile Ala Tyr Glu Thr Val Gln Thr Ala Asp Gly Ala
        115                 120                 125
```

-continued

Leu Pro Leu Leu Ala Pro Met Ser Glu Val Ala Gly Arg Leu Ala Ala
    130                 135                 140

Gln Val Gly Ala Tyr His Leu Met Arg Thr Gln Gly Gly Arg Gly Val
145                 150                 155                 160

Leu Met Gly Gly Val Pro Gly Val Glu Pro Ala Asp Val Val Ile
                165                 170                 175

Gly Ala Gly Thr Ala Gly Tyr Asn Ala Ala Arg Ile Ala Asn Gly Met
                180                 185                 190

Gly Ala Thr Val Thr Val Leu Asp Ile Asn Ile Asp Lys Leu Arg Gln
            195                 200                 205

Leu Asp Ala Glu Phe Cys Gly Arg Ile His Thr Arg Tyr Ser Ser Ala
    210                 215                 220

Tyr Glu Leu Glu Gly Ala Val Lys Arg Ala Asp Leu Val Ile Gly Ala
225                 230                 235                 240

Val Leu Val Pro Gly Ala Lys Ala Pro Lys Leu Val Ser Asn Ser Leu
                245                 250                 255

Val Ala His Met Lys Pro Gly Ala Val Leu Val Asp Ile Ala Ile Asp
                260                 265                 270

Gln Gly Gly Cys Phe Glu Gly Ser Arg Pro Thr Thr Tyr Asp His Pro
        275                 280                 285

Thr Phe Ala Val His Asp Thr Leu Phe Tyr Cys Val Ala Asn Met Pro
    290                 295                 300

Ala Ser Val Pro Lys Thr Ser Thr Tyr Ala Leu Thr Asn Ala Thr Met
305                 310                 315                 320

Pro Tyr Val Leu Glu Leu Ala Asp His Gly Trp Arg Ala Ala Cys Arg
                325                 330                 335

Ser Asn Pro Ala Leu Ala Lys Gly Leu Ser Thr His Glu Gly Ala Leu
            340                 345                 350

Leu Ser Glu Arg Val Ala Thr Asp Leu Gly Val Pro Phe Thr Glu Pro
        355                 360                 365

Ala Ser Val Leu Ala
        370

<210> SEQ ID NO 19
<211> LENGTH: 377
<212> TYPE: PRT
<213> ORGANISM: Enterobacter aerogenes

<400> SEQUENCE: 19

Met Ile Ile Gly Val Pro Lys Glu Ile Lys Asn Asn Glu Asn Arg Val
1               5                   10                  15

Ala Met Thr Pro Ala Gly Val Val His Leu Leu Asn Ala Gly His Lys
            20                  25                  30

Val Ile Ile Glu Thr Asn Ala Gly Leu Gly Ser Gly Phe Thr Asn Glu
        35                  40                  45

Glu Tyr Lys Gln Ala Gly Ala Glu Ile Ile Glu Ser Ala Ser Asp Val
    50                  55                  60

Trp Thr Lys Ala Asp Met Ile Met Lys Val Lys Glu Pro Leu Ala Ser
65                  70                  75                  80

Glu Tyr Gly Tyr Phe Arg Lys Gly Leu Ile Leu Phe Thr Tyr Leu His
                85                  90                  95

Leu Ala Ala Glu Pro Glu Leu Thr Lys Ala Leu Val Asp Ser Glu Val
            100                 105                 110

Ile Ala Ile Ala Tyr Glu Thr Val Thr Val Asn Arg Thr Leu Pro Leu
        115                 120                 125

```
Leu Ser Pro Met Ser Glu Val Ala Gly Arg Met Ala Ala Gln Val Gly
        130                 135                 140

Ala Gln Phe Leu Glu Lys Thr Gln Gly Gly Lys Gly Ile Leu Leu Ser
145                 150                 155                 160

Gly Val Pro Gly Val Lys Arg Gly Lys Val Thr Ile Ile Gly Gly Gly
                165                 170                 175

Met Val Gly Thr Asn Ala Ala Lys Ile Ala Val Gly Leu Gly Ala Asp
            180                 185                 190

Val Thr Ile Ile Asp Leu Asn Pro Asp Arg Leu Arg Gln Leu Glu Asp
        195                 200                 205

Ile Phe Gly Thr Ser Val Gln Thr Leu Met Ser Asn Pro Tyr Asn Ile
    210                 215                 220

Ala Glu Ala Val Lys Glu Ser Asp Leu Val Ile Gly Ser Val Leu Ile
225                 230                 235                 240

Pro Gly Ala Lys Ala Pro Lys Leu Val Thr Glu Glu Met Val Lys Ser
                245                 250                 255

Met Gln Pro Gly Ser Val Ile Val Asp Val Ala Ile Asp Gln Gly Gly
            260                 265                 270

Asn Phe Glu Thr Val Asp His Ile Thr Thr His Asp Asp Pro Thr Tyr
        275                 280                 285

Val Lys His Gly Val Val His Tyr Ala Val Ala Asn Met Pro Gly Ala
    290                 295                 300

Val Pro Arg Thr Ala Thr Ile Ala Leu Thr Asn Val Thr Ile Pro Tyr
305                 310                 315                 320

Ala Val Gln Ile Ala Thr Lys Gly Val Val Lys Ala Val Asn Asp Asn
                325                 330                 335

Pro Ala Ile Lys Ala Gly Val Asn Val Ala Asn Gly His Val Thr Phe
            340                 345                 350

Glu Ala Val Ala Asn Asp Leu Gly Tyr Lys Tyr Val Thr Val Glu Glu
        355                 360                 365

Ala Ile Ser Lys Glu Ala Ile Asn Ala
    370                 375

<210> SEQ ID NO 20
<211> LENGTH: 558
<212> TYPE: PRT
<213> ORGANISM: Pseudomonas putida

<400> SEQUENCE: 20

Met Tyr Asp Tyr Ile Ile Val Gly Ala Gly Ser Ala Gly Cys Val Leu
1               5                   10                  15

Ala Asn Arg Leu Ser Ala Asp Pro Ser Lys Arg Val Cys Leu Leu Glu
            20                  25                  30

Ala Gly Pro Arg Asp Thr Asn Pro Leu Ile His Met Pro Leu Gly Ile
        35                  40                  45

Ala Leu Leu Ser Asn Ser Lys Lys Leu Asn Trp Ala Phe Gln Thr Ala
    50                  55                  60

Pro Gln Gln Asn Leu Asn Gly Arg Ser Leu Phe Trp Pro Arg Gly Lys
65                  70                  75                  80

Thr Leu Gly Gly Ser Ser Ser Ile Asn Ala Met Val Tyr Ile Arg Gly
                85                  90                  95

His Glu Asp Asp Tyr His Ala Trp Glu Gln Ala Ala Gly Arg Tyr Trp
            100                 105                 110

Gly Trp Tyr Arg Ala Leu Glu Leu Phe Lys Arg Leu Glu Cys Asn Gln
```

-continued

```
            115                 120                 125
Arg Phe Asp Lys Ser Glu His His Gly Val Asp Gly Glu Leu Ala Val
    130                 135                 140

Ser Asp Leu Lys Tyr Ile Asn Pro Leu Ser Lys Ala Phe Val Gln Ala
145                 150                 155                 160

Gly Met Glu Ala Asn Ile Asn Phe Asn Gly Asp Phe Asn Gly Glu Tyr
                165                 170                 175

Gln Asp Gly Val Gly Phe Tyr Gln Val Thr Gln Lys Asn Gly Gln Arg
            180                 185                 190

Trp Ser Ser Ala Arg Ala Phe Leu His Gly Val Leu Ser Arg Pro Asn
        195                 200                 205

Leu Asp Ile Ile Thr Asp Ala His Ala Ser Lys Ile Leu Phe Glu Asp
210                 215                 220

Arg Lys Ala Val Gly Val Ser Tyr Ile Lys Lys Asn Met His His Gln
225                 230                 235                 240

Val Lys Thr Thr Ser Gly Gly Glu Val Leu Leu Ser Leu Gly Ala Val
                245                 250                 255

Gly Thr Pro His Leu Leu Met Leu Ser Gly Val Gly Ala Ala Ala Glu
            260                 265                 270

Leu Lys Glu His Gly Val Ser Leu Val His Asp Leu Pro Glu Val Gly
        275                 280                 285

Lys Asn Leu Gln Asp His Leu Asp Ile Thr Leu Met Cys Ala Ala Asn
            290                 295                 300

Ser Arg Glu Pro Ile Gly Val Ala Leu Ser Phe Ile Pro Arg Gly Val
305                 310                 315                 320

Ser Gly Leu Phe Ser Tyr Val Phe Lys Arg Glu Gly Phe Leu Thr Ser
                325                 330                 335

Asn Val Ala Glu Ser Gly Gly Phe Val Lys Ser Ser Pro Asp Arg Asp
            340                 345                 350

Arg Pro Asn Leu Gln Phe His Phe Leu Pro Thr Tyr Leu Lys Asp His
        355                 360                 365

Gly Arg Lys Ile Ala Gly Gly Tyr Gly Tyr Thr Leu His Ile Cys Asp
    370                 375                 380

Leu Leu Pro Lys Ser Arg Gly Arg Ile Gly Leu Lys Ser Ala Asn Pro
385                 390                 395                 400

Leu Gln Pro Pro Leu Ile Asp Pro Asn Tyr Leu Ser Asp His Glu Asp
                405                 410                 415

Ile Lys Thr Met Ile Ala Gly Ile Lys Ile Gly Arg Ala Ile Leu Gln
            420                 425                 430

Ala Pro Ser Met Ala Lys His Phe Lys His Glu Val Val Pro Gly Gln
        435                 440                 445

Ala Val Lys Thr Asp Asp Glu Ile Ile Glu Asp Ile Arg Arg Arg Ala
    450                 455                 460

Glu Thr Ile Tyr His Pro Val Gly Thr Cys Arg Met Gly Lys Asp Pro
465                 470                 475                 480

Ala Ser Val Val Asp Pro Cys Leu Lys Ile Arg Gly Leu Ala Asn Ile
                485                 490                 495

Arg Val Val Asp Ala Ser Ile Met Pro His Leu Val Ala Gly Asn Thr
            500                 505                 510

Asn Ala Pro Thr Ile Met Ile Ala Glu Asn Ala Ala Glu Ile Ile Met
        515                 520                 525
```

```
Arg Asn Leu Asp Val Glu Ala Leu Glu Ala Ser Ala Glu Phe Ala Arg
    530                 535                 540

Glu Gly Ala Glu Leu Glu Leu Ala Met Ile Ala Val Cys Met
545                 550                 555
```

BIOTECHNOLOGICAL PRODUCTION OF ALCOHOLS AND DERIVATIVES THEREOF

CROSS REFERENCE TO RELATED APPLICATIONS

The present application is a continuation of U.S. patent application Ser. No. 14/367,610, filed on Jun. 20, 2014, now abandoned, which is a 35 U.S.C. § 371 national stage patent application of International patent application PCT/EP2012/075587, filed on Dec. 14, 2012, published as WO/2013/092426 on Jun. 27, 2013, the text of which is incorporated by reference, and claims the benefit of the filing date of European application no. EP11195222.2, filed on Dec. 22, 2011, the text of which is also incorporated by reference.

The present invention relates to a microorganism having a reduced fatty acid degradation capacity and expressing a recombinant alkane oxidase, a method for oxidizing an alkyl, comprising a contacting the alkyl with an aqueous solution comprising the inventive cell.

Industrial production of bulk and fine chemicals based on renewably resources such as biomass has a range of shortcomings. One of them is the need to extract from a large volume of aqueous medium the product of interest, a procedure necessary not only to concentrate the product for further downstream processing but also to limit its concentration in an aqueous medium typically comprising live cells. Such cells are extremely potent but nonetheless delicate catalysts which cannot be subjected to harsh conditions, for example high temperatures, extreme values of pH, the presence of hazardous solvents, products and the like, or else there is the chance that they might lyse to the effect that their catalytic activity is lost and cell debris, metabolites and macromolecules are released that may contaminate or even degrade the sought-after product.

In order to extract the product of interest, the aqueous medium is typically contacted with a comparably small volume of a water-immiscible organic solvent. As a result, a product having sufficiently high a degree of hydrophobicity is released from the aqueous culture medium and accumulates in the water-immiscible solvent. The product may subsequently be subjected to further synthetic steps compatible with the water-immiscible solvent or may be purified, for example by way of distillation or crystallization.

Whether or not a compound may be extracted from an aqueous phase using a water-immiscible organic solvent depends on its physicochemical properties. While compounds rich in or entirely consisting of unsubstituted carbon chains are likely to enter the solvent, compounds having functional groups comprising heteroatoms or even charges should be expected to prevail in the aqueous phase.

A compound's relative distribution in a liquid biphasic system which has reached the equilibrium state may be described using the Nernst distribution law:

$$\alpha = c_{Phase\ 1}/c_{Phase\ 2},$$

wherein $c_1$ and $c_2$ are the molar equilibrium concentrations of the compound in the first and second phase, respectively, and the constant k is a temperature-dependent distribution coefficient. The distribution properties of a compound may also described using the $K_{ow}$ or P value, in case the biphasic system comprises an aqueous phase and a phase comprising octanol:

$$K_{ow} = P = c_{Octanol}/c_{Water}.$$

These equations describe the distribution of a compound in a given liquid biphasic system, however, they apply only when the distribution equilibrium has been reached. If pure water and a pure water-immiscible organic solvent, for example water and hexane, are mixed, two distinct phases will emerge almost instantly. However, the situation is very different if an aqueous culture medium comprising a live cell and a water-immiscible solvent are contacted. Owing to the numerous possible molecular interactions, separation of the water-immiscible solvent may take several hours if not days; meanwhile the cells are subjected to contact with the potentially toxic solvent. Hence, the time taken for the biphasic state to be reached is a parameter that should be optimised if an efficient process for the biotechnological production of chemicals is to be devised.

Substituted alkanes, for example alcohols, aldehydes, ketones, carboxylic acids and amines, represent of a class of industrially sought-after compounds traditionally prepared by conversion of compounds made from fossil carbon sources. In an era of increasingly limiting supplies of non-renewable fossil fuels, there is considerable interest in biotechnological processes for producing alkanes and derivates thereof starting with renewable resources, i.e. materials that are easily and, in terms of geological time scales, rapidly replenishable.

Numerous methods for converting an alkane into a corresponding substituted alkane, in particular an oxidised alkanes, have been reported in the prior art. Methane monooxygenases catalyse the NADH-dependent insertion of one atom of oxygen into the C—H bond of methane to form methanol, the first step in the degradation of methane by methanotrophs such as *Methylosinus trichosporium* and *Methylococcus capsulatus*. The soluble methane monooxygenases typically have a broad substrate spectrum including saturated and unsaturated, linear, branched, and cyclic hydrocarbons up to about C8, as well as aromatic, heterocyclic, and chlorinated compounds (Merkx M, Kopp D A, Sazinsky M H, Blazyk J L, Müller J, Lippard S J (2001), Angew Chem Int Ed Engl 40:2782-2807; Higgins I J, Best D J, Hammond R C. 1980. New findings in methane-utilizing bacteria highlight their importance in the biosphere and their commercial potential. Nature 286:561-564). Heme-containing oxygenases, most notably those from the class of cytochrome P450 systems including cytochrome P450 BM-3 from *Bacillus megaterium*, also use molecular oxygen in order to hydroxylate alkanes of various carbon chain lengths and have been subjected to protein evolution approaches (Koch D J, Chen, M M, van Beilen, J. B. and Arnold F. H. (2009, Appl. And Environm. Microbiol. 75(2), 337-344). Rubredoxin-dependent alkane monoxygenases such as the alkane monooxygenase from *Pseudomonas putida* GPo1 catalyse the oxidation of alkanes of medium chain lengths, yielding a mixture of alcohols and carboxylic acids (Grant C., Woodley, J. M, and Baganz, F (2011) Enzyme and Microbial Technology 48, 480-486). Xylene monooxygenases hydroxylate alkanes which may subsequently be converted to various other substituted alkanes including amines, carboxylic acids, amides, alkyl halides, esters, alkenes, using biotechnological or synthetic approaches (Bruce, P. Y. (1998), Organic Chemistry, Sec. Ed., Prentic Hall Inc.).

Alkanes consist only of hydrogen and carbon atomes bonded by single bonds and as such lack functional groups comprising heteroatoms. Consequently, even short alkanes substituted with a polar functional group, let alone those comprising long unsubstituted carbon chains, are soluble in water-immiscible organic solvents. Last but not least, many of them, for example methanol and ethanol, are reactive and are known to have adverse effects on the growth, viability and metabolism of biotechnologically relevant microorganisms. Therefore, many biotechnological processes for the production of such compounds comprise an extraction step using water-immiscible solvents.

Therefore, the problem underlying the present invention is to provide a biotechnological process for converting an alkane to a substituted alkane in a biphasic system comprising an aqueous medium and a water-immiscible solvent, wherein the separation of the water-immiscible solvent from the aqueous medium is rapid. More specifically, the problem underlying the present invention is to improve the separation of a water-immiscible solvent and a substituted alkane solved therein in terms of the time taken to separate the two phases, the degree of separation of the solvent in a given time, yield and purity of the product solved therein or obtained following further processing as well as viability and/or recyclability of any cells contacted with the water-immiscible solvent.

Another problem underlying the present invention is to provide a cell that may be used for such a process, preferably one that is more resistant towards stress caused by the presence of water-immiscible organic solvents, for example in terms of oxygen consumption, oxygen consumption per amount of product, growth rates, metabolic activity and viability in general.

Another problem underlying the present invention is to set up a process for producing oxidation products of alkanes and derivatives thereof based and sustainable resources.

Another problem underlying the present invention is to provide a biotechnological process for oxidizing alkanes, wherein the consumption of oxygen is reduced.

The problem underlying the present invention is solved by the subject matter of the attached claims.

The problem underlying the present invention is solved, in a first aspect, by a microorganism having a reduced fatty acid degradation capacity and expressing a recombinant alkane oxidase.

In a first embodiment of the first aspect, the alkane oxidase is selected from the group comprising rubredoxin-dependent alkane oxidases, cytochrome P450 alkane oxidases, xylene monooxygenases, methane monooxygenases and variants thereof.

In a second embodiment, which is also an embodiment of the first embodiment of the first aspect of the present invention, the fatty acid degradation capacity is reduced by deletion of a gene encoding an enzyme from the group comprising fatty acid importer, fatty acid-CoA ligase, acyl-CoA dehydrogenase, 2,4-dienoyl-CoA reductase, enoyl-CoA hydratase and 3-ketoacyl-CoA thiolase.

In a third embodiment, which is also an embodiment of the first and the second embodiment of the first aspect of the present invention, the microorganism is a prokaryotic or a lower eukaryotic cell, preferably a bacterial cell, most preferably E. coli.

In a fourth embodiment, which is also an embodiment of the first to third embodiments of the first aspect of the present invention, the microorganism further expresses a recombinant alcohol dehydrogenase.

In a fifth embodiment, which is also an embodiment of the first to fourth embodiments of the first aspect of the present invention, the microorganism further expresses a recombinant transaminase.

In a sixth embodiment, which is also an embodiment of the first to fifth embodiments of the first aspect of the present invention, the microorganism expresses a recombinant amino acid dehydrogenase, preferably an alanine dehydrogenase.

The problem underlying the present invention is solved, in a second aspect, by a method for oxidising an alkyl, comprising a) contacting the alkyl with an aqueous solution comprising the cell according to the first aspect of the present invention and any of its embodiments.

In a first embodiment of the second aspect of the present invention, the problem is solved by a method further comprising b) contacting the aqueous solution from step a) with a water-immiscible organic solvent.

In a second embodiment of the second aspect of the present invention which is also an embodiment of the first embodiment, the extraction is carried out following completion of the alkyl oxidation and preferably removal of the inventive cell from the aqueous solution.

The problem underlying the present invention is solved, in a third aspect, by a use of the microorganism according to the first aspect and any of its embodiments for oxidising an alkyl.

In a further embodiment of the second or third aspect or any of its embodiments, the alkyl is a compound represented by the formula H—$(CH_2)_x$—R, wherein x is 1 to 30, and R is any chemical group, preferably one selected from the group comprising —OH, —COH, —COOH, —COOR$^1$, —NH$_2$, —NO$_2$, —CN, —OPO$_3$H, —SO$_3$H and —H, and is preferably H, and wherein R$^1$ is an unsubstituted linear alkyl, preferably methyl and ethyl.

In a further embodiment of the second or third aspects or any of their embodiments, the alkyl is a linear alkane, preferably one that is gaseous at room temperature.

In a further embodiment of the second or third aspects of the invention and any of their embodiments, the water-immiscible organic solvent is a water-immiscible fatty acid or fatty acid ester.

The inventors of the present invention have surprisingly found that the separation of a water-immiscible organic solvent from an aqueous culture medium comprising a microorganism capable of catalyzing alkane or alkyl oxidation is more rapid and complete if a microorganism having a reduced fatty acid degradation capacity rather than a corresponding wild type microorganism is used.

Moreover, the present inventors have found that microorganisms having a reduced fatty acid degradation capacity consume less oxygen relative to the respective wild type microorganisms while the yield of the product is equal or even improved.

Without wishing to be bound by any theory, the inventors of the present invention theorise that reducing the fatty acid degradation capacity of a cell leads to lowered levels of at least one as yet unidentified metabolite acting as a detergent and counteracting separation of a water-immiscible organic solvent, located either intracellularly or at the surface of the cell of interest.

The present invention contemplates a method for oxidising an alkyl. The alkyl may be oxidised to one or more compounds selected from the group comprising an alcohol, an aldehyde, a ketone, and a carboxylic acid. Such a compound may be the main product of an inventive process, but it may also be further processed. For example, the method may not only comprise the oxidation of an alkyl to a carboxylic acid, but also the conversion of such a carboxylic acid to an amide.

The present invention centers around a microorganism having a reduced fatty acid degradation capacity and expressing a recombinant alkane oxidase, preferably for the conversion of alkyls to oxidized alkyls such as alcohols. In a preferred embodiment, the term "alkane oxidase", as used herein, refers to any enzyme capable of oxidizing an alkane and/or alkyls. Various alkane oxidases have been described in the literature, for example basidiomycete heme-thiolate peroxidases (Gutierrez, A., Babot, E. D., Ullrich, R., Hofrichter, M., Martinez, A. T., del Rio, J. C. (2011), Arch. Biochem. Biophys. 514 (1-2), 33-43), the alkane hydroxylase system of *Gardonia* sp. strain SoCg (Lo Piccolo, L., De Pasquale, C., Fodale, R., Puglia, A. M., Quatrini, P. (2011), Appl. Environm. Microbiol. 77 (4), 1204-12013; Alkane oxidases from *Alcanivorax* (Grant, C., Woodley, J. M., Baganz, F. (2011) Enzyme and Microbial Technology, 480-486) and Cytochrom P450 systems (Koch, D. J., Chen, M. M., van Beilen, J. B., and Arnold F. H. (2009) *Appl. and Env. Microbiology*, 337-344). In a particularly preferred embodiment, the alkane oxidase is an alkB type alkane oxidase. AlkB is an oxidoreductase from the *Pseudomonas putida* AlkBGT system, dependent on two auxiliary polypeptides, AlkG and AlkT. AlkT is a FAD-dependent rubredoxin reductase transferring electrons from NADH to AlkG. AlkG is a rubredoxin, an iron-containing redox protein functioning as a direct electron donor to AlkB. In a preferred embodiment, the term "alkB type alkane oxidase", as used herein, refers to AlkB from *Pseudomonas putida* Gpo1 (Access code: CAB54050.1 (SEQ ID NO:1), any access code used in the application refers to the respective sequence from the Genbank database run by the NCBI, wherein the release referred to is the one online on the 15 Dec. 2011) or a variant thereof. In a preferred embodiment, the term "alkyl" refers to a substituent represented by the formula H—$(CH_2)_x$—R, wherein R is any chemical group and x is 1, 2, 3, . . . , preferably 8 or more, more preferably 11 or more, or to a compound comprising such a substituent.

In a preferred embodiment, the term "rubredoxin-dependent alkane oxidase", as used herein refers to an oxidoreductase that recognises as its substrate an alkane receiving electrons via a rubredoxin, the latter being, in a more preferred preferred embodiment, an iron-sulphur protein having an α+β class fold with 2 α helices and 2 to 3 β-strands transferring electrons to the alkane oxidase and is, in a most preferred embodiment, AlkG from *Pseudomonas putida* or a variant thereof. Examples include AlkG from *Pseudomonas putida*.

In a preferred embodiment, the term "cytochrome P450 enzyme", as used herein, refers to an oxidoreductase having a P450-type cytochrome having, in its CO-bound form an absorption band at 450 nm and preferably capable of oxidizing an alkane. Examples include cytochrome P450 BM-3 from *Bacillus megaterium* (Koch, D. J., Chen, M. M., van Beilen, J. B., and Arnold, F. H. (2009) *Appl. And Environm. Microbiol.* 75(2), 337-344).

In a preferred embodiment, the term "xylene monooxygenase", as used herein, refers to a membrane-spanning, non-heme diiron enzyme oxidoreductase with a histidine-rich active site and preferably capable of oxidizing an alkane. Examples include XylM from *Pseudomonas putida* (Austin, R. N., Buzzi, K., Kim, E., Zylstra, G. J., and Groves, J. T. (2003) *J. Biol. Inorg. Chem.* 8, 733-740.

In a preferred embodiment, the term "methane monooxygenase", as used herein, refers to an oxidoreductase that is either a soluble methane monooxygenase comprising di-iron center bridged by an oxygen atom (Fe—O—Fe) and comprising three protein components, a hydroxylase, a β unit, and a reductase, from a methanotropic bacterium or is a particulate methane monooxygenase, a membrane-protein in a methanotrophic bacterium, comprising a copper-containing active site. Examples of soluble and particulate methane monooxygenases comprises the soluble methane monooxygenase from *Methylosinus trichosporium* OB3b (A C Rosenzweig, Frederick, C. A., Lippard, S. J., Nordlung, P. (1993) Nature, 366, 537-543) and the particulate methane monooxygenase from *Methylococcus capsulatus* (Bath) (Nguyen, H. H. T., Elliot, S. J., Yip, J. H. K, and Chan, S. I. (1998), *J. Biol. Chem.* 273, 7957-7966), respectively.

The teachings of the present invention may not only carried out using biological macromolecules having the exact amino acid or nucleic acid sequences referred to in this application explicitly, for example by name or accession number, or implicitly, but also using variants of such sequences. In a preferred embodiment, the term "variant", as used herein, comprises amino acid or nucleic acid sequences, respectively, that are 70, 75, 80, 85, 90, 92, 94, 95, 96, 97, 98 or 99% identical to the reference amino acid or nucleic acid sequence, wherein preferably amino acids other than those essential for the function, for example the catalytic activity of a protein, or the fold or structure of a molecule are deleted, substituted or replaced by insertions or essential amino acids are replaced in a conservative manner. The state of the art comprises algorithms that may be used to align two given nucleic acid or amino acid sequences and to calculate the degree of identity, see Arthur Lesk (2008), Introduction to bioinformatics, 3$^{rd}$ edition, Thompson et al., Nucleic Acids Research 22, 4637-4680, 1994, and Katoh et al., Genome Information, 16(1), 22-33, 2005. The term "variant" is used synonymously and interchangeably with the term "homologue". Such variants may be prepared by introducing deletions, insertions or substitutions in amino acid or nucleic acid sequences as well as fusions comprising such macromolecules or variants thereof. In a preferred embodiment, the term "variant", with regard to amino acid sequence, comprises, preferably in addition to the above sequence identity, amino acid sequences that comprise one or more conservative amino acid changes with respect to the respective reference or wild type sequence or comprises nucleic acid sequences encoding amino acid sequences that comprise one or more conservative amino acid changes. In a preferred embodiment, the term "variant" of an amino acid sequence or nucleic acid sequence comprises, preferably in addition to the above degree of sequence identity, any active portion and/or fragment of the amino acid sequence or nucleic acid sequence, respectively, or any nucleic acid sequence encoding an active portion and/or fragment of an amino acid sequence. In a preferred embodiment, the term "active portion", as used herein, refers to an amino acid sequence or a nucleic acid sequence, which is less than the full length amino acid sequence or codes for less than the full length amino acid sequence, respectively, wherein the amino acid sequence or the amino acid sequence encoded, respectively retains at least some of its essential biological activity. For example an active portion and/or fragment of a protease is capable of hydrolysing peptide bonds in polypeptides. In a preferred embodiment, the term "retains at least some of its essential biological activity", as used herein, means that the amino acid sequence in question has a biological activity exceeding and distinct from the background activity and the kinetic parameters characterising said activity, more specifically $k_{cat}$ and $K_M$, are preferably within 3, more preferably 2, most preferably one order of magnitude of the values displayed by the reference molecule with respect to a specific substrate. In a preferred embodiment, the term "variant" of a nucleic acid comprises nucleic acids the complementary strand of which hybridises, preferably under stringent conditions, to the reference or wild type nucleic acid. Stringency of hybridisation reactions is readily determinable by one of ordinary skilled in the art, and in generally is an empirical calculation dependent on probe length, washing temperature and salt concentration. In general longer probes require higher temperatures for proper annealing, while shorter probes need lower temperatures. Hybridisation generally depends on the ability of denatured DNA to reanneal to complementary strands are present in an environment below their melting temperature. The higher the degree of desired homology between the probe and hybridisable sequence, the higher the relative temperature which may be used. As a result it follows that higher relative temperatures would tend to make the reaction conditions more stringent, while lower temperature less so. For additional details and explanation of stringency of hybridisation reactions, see F. M. Ausubel (1995), Current Protocols in Molecular Biology. John Wiley & Sons, Inc. Moreover, the person skilled take in the art may follow the instructions given in the manual "The DIG System Users Guide for Filter Hybridization", Boehringer Mannheim GmbH, Mannheim, Germany, 1993 and in Liebl et al. (International Journal of Systematic Bacteriology 41: 255-260 (1991) on how to identify DNA sequences by means of hybridisation. In a preferred embodiment, stringent conditions are applied for any hybridisation, i.e. hybridisation occurs only if the probe is 70% or more identical to the target sequence. Probes having a lower degree of identity with respect to the target sequence may hybridise, but such hybrids are unstable and will be removed in a washing step under stringent conditions, for example lowering the concentration of salt to 2×SSC or, optionally and subsequently, to 0.5×SSC, while the temperature is, in order of increasing preference, approximately 50° C.-68° C., approximately 52° C.-68° C., approximately 54° C.-68° C., approximately 56° C.-68° C., approximately 58° C.-68° C., approximately 60° C.-68° C., approximately 62° C.-68° C., approximately 64° C.-68° C., approximately 66° C.-68° C. In a particularly preferred embodiment, the temperature is approximately 64° C.-68° C. or approximately 66° C.-68° C. It is possible to adjust the concentration of salt to 0.2×SSC or even 0.1×SSC. Polynucleotide fragments having a degree of identity with respect to the reference or wild type sequence of at least 70, 80, 90, 91, 92, 93, 94, 95, 96, 97, 98, 99% may be isolated. In a preferred embodiment, the term "homologue" of a nucleic acid sequence, as used herein, refers to any nucleic acid sequence that encodes the same amino acid sequence as the reference nucleic acid sequence, in line with the degeneracy of the genetic code.

The inventive teachings may be carried out using a wide range of microorganisms. In a preferred embodiment, the term "microorganism", as used herein, refers to any permanently unicellular microorganism comprising bacteria archaea, fungi, algae and the like. In a preferred embodiment, the microorganism is a bacterial microorganism, more preferably one from the group comprising *Pseudomonas, Corynebacterium* and *Escherichia*, most preferably *Escherichia coli*. In another preferred embodiment, the microorganism is a lower eukaryote, more preferably a fungi from the group comprising *Saccharomyces, Candida, Picchia, Schizosaccharomyces* and *Yarrowia*, and is most preferably *Saccharomyces cerivisiae*. Throughout this application, the term "microorganism" is used synonymously and interchangeably with the term "cell". The microorganism may be an isolated microorganism, in other words a pure culture of a single strain of microorganism, or may comprise a mixture of at least two strains. Biotechnologically relevant microorganisms are commercially available, for example from the American Type Culture Collection (ATCC) or the German Collection of Microorganisms and Cell Cultures (DSMZ). Particles for keeping and modifying microorganisms are available from the prior art, for example *Sambroke/Fridge/Maniadis* (1989): *Molecular cloning—A Laboratory Manual*, Cold Spring Harbour Press, $2^{nd}$ edition, Fuchs/Schlegel (2007), *Allgemeine Mikrobiologie*, 2008, Georg Thieme Verlag.

The inventive microorganism has a reduced fatty acid degradation capacity. In a preferred embodiment, the term "having a reduced fatty acid degradation capacity", as used in herein, means that the respective microorganism degrades fatty acids, preferably those taken up from the environment, at a lower rate than a comparable microorganism having normal fatty acid degradation capacity would. In a preferred embodiment, the fatty acid degradation of such a microorganism is lower on account of deletion, inhibition or inactivation of at least one gene encoding an enzyme involved in the β-oxidation pathway. In a preferred embodiment of the present invention, at least one enzyme involved in the β-oxidation pathway has lost, in order of increasing preference, 5, 10, 20, 40, 50, 75, 90 or 99% activity relative to the activity of the same enzyme under comparable conditions in the respective wild type microorganism. The person skilled in the art is familiar with various techniques that may be used to delete a gene encoding an enzyme or reduce the activity of such an enzyme in a microorganism, for example by exposition of cells to radioactivity followed by accumulation or screening of the resulting mutants, site-directed introduction of point mutations or knock out of a chromosomally integrated gene encoding for an active enzyme, as described in Sambrook/Fritsch/Maniatis (1989). In addition, the transcriptional repressor FadR may be over expressed to the effect that expression of enzymes involved in the β-oxidation pathway is repressed (Y Fujita, H Matsuoka, and K Hirooka (2007) *Mol. Microbiology* 66(4), 829-839). In a preferred embodiment, the term "deletion of a gene", as used herein, means that the nucleic acid sequence encoding said gene is modified such that the expression of active polypeptide encoded by said gene is reduced. For example, the gene may be deleted by removing in-frame a part of the sequence comprising the sequence encoding for the catalytic active centre of the polypeptide. Alternatively, the ribosome binding site may be altered such that the ribosomes no longer translate the corresponding RNA. Moreover, the person skilled in the art is able to routinely measure the activity of enzymes expressed by living cells using standard essays as described in enzymology text books, for example A Cornish-Bowden (1995), Fundamentals of Enzym Kinetics, Portland Press Limited, 1995. The state of the art discloses various tests designed specifically for determining the activity of enzymes involved in the β-oxidation pathway, for example K Kameda & W D Nunn (1981) J. Biol. Chem. 256, 5702-5707, H Marrakchi, W E DeWolf, C Quinn, J West, B J Polizzi, C Y So et al. (2003) Biochem. J. 370, 1055-1062, S Lobo, G Florova, and K A Reynolds (2001) Biochemistry 40 (39), 11955-64, X Yu, T Liu, F Zhu, and C Khosla (2011) PNAS, published online).

Degradation of fatty acids in microorganisms is accomplished by a sequence of enzymatically catalysed reactions. First of all, fatty acids are taken up and translocated across the cell membrane via a transport/acyl-activation mechanism involving at least one outer membrane protein and one inner membrane-associated protein which has fatty acid-CoA ligase activity, referred to in the case of *E. coli* as FadL and FadD, respectively. Inside the cell, the fatty acid to be degraded is subjected to enzymes catalyzing other reactions of the β-oxidation pathway. The first intracellular step involves the conversion of acyl-CoA to enoyl-CoA through acyl-CoA dehydrogenase, the latter referred to as FadE in the case of *E. coli*. The resulting enoyl-CoA is converted to 3-ketoacyl-CoA via 3-hydroxylacyl-CoA through hydration and oxidation, catalysed be enoyl-CoA hydratase/3-hydroxyacyl-CoA dehydrogenase, referred to as FadB in *E. coli*. Finally, 3-ketoacyl-CoA thiolase, FadA in *E. coli*, catalyses the cleavage of 3-ketoacyl-CoA, to give acetyl-CoA and the input acyl-CoA shortened by two carbon atoms. In a preferred embodiment, the term "a microorganism having a reduced fatty acid degradation capacity", as used herein, refers to a microorganism having a reduced capability of taking up and/or degrading fatty acids, preferably those having at least eight carbon chains. The fatty acid degradation capacity of a microorganism may be reduced in various ways. In a preferred embodiment, the microorganism has, compared to its wild type, a reduced activity of an enzyme involved in the β-oxidation pathway. In a preferred embodiment, the term "enzyme involved in the β-oxidation pathway", as used herein, refers to an enzyme that interacts directly with a fatty acid or a derivative thereof formed as part of the degradation said fatty acid via the β-oxidation pathway the sequence of reactions effecting the conversion of a fatty acid to acetyl-CoA and the CoA ester of the shortened fatty acid, preferably by recognizing the fatty acid or derivative thereof as a substrate, and converts it to a metabolic formed as a part of the β-oxidation pathway. In a particularly preferred embodiment, the term "enzyme involved in the β-oxidation pathway" includes a fatty acid importer, more specifically any component of the fatty acid import machinery such as FadL or variants thereof and a membrane-bound fatty acid CoA-ligase. For example, the acyl-CoA dehydrogenase is an enzyme involved in the β-oxidation pathway as it interacts with fatty acid-CoA and converts fatty acid-CoA ester to enoyl-CoA, which is a metabolite formed as part of the β-oxidation. In a preferred embodiment, the term "enzyme involved in the fatty inter oxidation pathway", as used herein, comprises any polypeptide from the group comprising fatty acid importer and components thereof, fatty acid CoA-ligase, acyl-CoA dehydrogenase, enoyl-CoA hydratase, 3-hydroxyacyl-CoA dehydrogenase and 3-keto-acyl-CoA thiolase. In a preferred embodiment, the term "fatty acid transporter", as used herein, refers to a polypeptide capable of translocating a fatty acid from the outer side of the membrane or outer, i.e. medium-exposed membrane, membrane of a microorganism into the inside of the cell, possibly as part of a machinery comprising several active polypeptides. For example, the polypeptide FadL (access code: BAA16205.1 (SEQ ID NO: 2)) in *E. coli* is a fatty acid transporter. In a preferred embodiment, the term "fatty acid-CoA ligase", as used herein, refers to a polypeptide capable of catalysing the conversion a fatty acid to the CoA ester of a fatty acid, i.e. a molecule, wherein the functional group —OH of the carboxy group is replaced with —S-CoA, preferably for introducing said fatty acid into the β-oxidation pathway. For example, the polypeptide FadD in *E. coli* (access code: BAA15609.1 (SEQ ID NO:3)) is an acyl-CoA dehydrogenase. In a preferred embodiment, the term "acyl-CoA dehydrogenase", as used herein, is a polypeptide capable of catalysing the conversion of an acyl-CoA to enoyl-CoA, preferably as part of the β-oxidation pathway. For example, the polypeptide FadE in *E. coli* (access code: BAA77891.2 (SEQ ID NO:4)) is an acyl-CoA dehydrogenase. In a preferred embodiment, the term "2,4-dienoyl-CoA reductase", as used herein, is a polypeptide capable of catalysing the conversion of the 2,4-dienoyl CoA from an unsaturated fatty acid into enoyl-CoA, preferably as part of the β-oxidation pathway. For example, the polypeptide FadH in *E. coli* is a 2,4-dienoyl-CoA reductase. In a preferred embodiment, the term "enoyl-CoA hydratase", as used herein, also referred to as 3-hydroxyacyl-CoA dehydrogenase, refers to a polypeptide capable of catalysing the conversion of enoyl-CoA to 3-ketoacyl-CoA through hydration and oxidation, preferably as part of the β-oxidation pathway. For example, the polypeptide FadB in *E. coli* (access code: BAE77457.1 (SEQ ID NO:5)) is an enoyl-CoA hydratase. In a preferred embodiment, the term "ketoacyl-CoA thiolase", as used herein, refers to a polypeptide capable of catalysing the conversion of cleaving 3-ketoacyl-CoA, resulting in an acyl-CoA shortened by two carbon atoms and acetyl-CoA, preferably as the final step of the b-oxidation pathway. For example, the polypeptide FadA in *E. coli* (access code: AP009048.1 (SEQ ID NO:6)) is a ketoacyl-CoA thiolase.

A multitude of compounds may be converted to an alcohol using the inventive microorganism, as long as they comprise an alkyl substituent, including, but not limited to alkanes, alkenes, alkynes, aryls, heteroaryls, alcohols, amines, alkanoic acids, alkenoic acids, lipids, amino acids, saturated or unsaturated and/or linear or branched fatty acids. In a preferred embodiment, the term "alkyl", as used herein, is a compound represented by the formula H—$(CH_2)_x$—R, wherein x is 4, 5, 6, 7, 8, 9, 10, 11, 12, 13, 14, 15, 16, 17, 18, 19, 20, 22, 24, 26, 28 or, in order of increasing preference, at least 6, 8, 10 or 12, and R is any chemical group, preferably one selected from the group comprising —OH, —COH, —COOH, —COOR$^1$, wherein R$^1$ is an unsubstituted linear alkyl, preferably Methyl and Ethyl, —NH$_2$, —NO$_2$, —CN, —OPO$_3$H, —SO$_3$H and —H, and is preferably H. In a preferred embodiment, the alkyl is a fatty acid or an ester thereof. In an other preferred embodiment, the alkyl is an alkane represented by the formula $C_nH_{2n+2}$ including branched alkanes, cycloalkanes and cycloalkanes having one or more linear alkyl substituents, and n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 and preferably 1 to 12, more preferably 1 to 4. In another preferred embodiment, the alkyl is an alkyl gaseous at 25° C. and under atmospheric pressure, including branched alkyls. In a preferred embodiment the alkane is isobutane.

It may be advantageous to use a microorganism that has, in addition to the recombinant alkane oxidase, further enzymes, preferably recombinant enzymes. In a preferred embodiment, the microorganism has, in addition to the alkane oxidase, a wild type or, preferably recombinant, alcohol dehydrogenase. In a preferred embodiment, the term "alcohol dehydrogenase", as used herein, refers to an enzyme capable of catalyzing the conversion of an alcohol to the corresponding aldehyde or ketone. Examples include, but are not limited to the alcohol dehydrogenases from *Bacillus stearothermophilus* (access code P42328 (SEQ ID NO: 7)), *Rhodococcus ruber* (access code AJ491307.1 (SEQ ID NO:8)), *Ralstonia eutropha* (access code ACB78191.1 (SEQ ID NO:9)), *Lactobacillus brevis* (access code YP_795183.1 (SEQ ID NO: 10)), *Lactobacillus kefiri* (access code ACF95832.1 (SEQ ID NO:11)), *Paracoccus pantotrophus* (access code ACB78182.1 (SEQ ID NO: 12)) and *Sphingobium yanoikuyae* (access code EU427523.1 (SEQ ID NO: 13)) as well as variants thereof.

The inventive microorganism may have, in addition to an alkane oxidase and an alcohol dehydrogenase, a transaminase, preferably a recombinant transaminase, which is advantageous if the aim is to convert an alkyl into an amine. In a preferred embodiment, the term "transaminase", as used herein, refers to an enzyme capable of transferring α-amino groups from a donor, preferably an amino acid, to an acceptor molecule, preferably an α-keto acid, to yield another amino acid. In a particularly preferred embodiment, the transaminase is a w-transaminase. Examples of transaminases include, but are not limited to the transaminase from *Chromobacterium violaceum* ATCC 12472 (access code NP_901695 (SEQ ID NO:14)).

The inventive microorganism may have, in addition to an alkane oxidase, an alcohol dehydrogenase and a transaminase, an amino acid dehydrogenase preferably a recombinant amino acid dehydrogenase. In a preferred embodiment, the term "alanine dehydrogenase", as used herein, refers to an enzyme capable of catalysing the conversion of an amino acid, water and NAD$^+$ to a keto acid, ammonia and NADH. The amino acid dehydrogenase may be an alanine dehydrogenase, i.e. an enzyme capable of catalysing the conversion of L-alanine, water and NAD$^+$ to pyruvate, ammonia and NADH. Examples of suitable amino acid dehydrogenases comprise alanine dehydrogenases from *Bacillus subtilis* (access code L20916 (SEQ ID NO:15)), *Rhizobium leguminosarum* (access code: CP001622 (SEQ ID NO:16)), *Vibrio proteolyticus* (access code: AF070716 (SEQ ID NO:17)), *Mycobacterium tuberculosis* (access code: X63069 (SEQ ID NO:18)) and *Enterobacter aerogenes* (access code AB013821 (SEQ ID NO:19)).

The inventive method comprises contacting the alkyl with an aqueous solution comprising the inventive cell. This step may not only comprise temporarily contacting the alkyl with the solution, but in fact incubating the alkyl in the presence of the inventive cell sufficiently long to allow for an oxidation reaction and possible further downstream reactions to occur, for example for at least 1, 2, 4, 5, 10 or 20 hours. The temperature chosen must be such that the inventive cells remains catalytically competent and/or metabolically active, for example 10 to 42° C., preferably 30 to 40° C., most preferably 32 to 38° C. in case the inventive cell is an *E. coli* cell.

In an embodiment, the inventive method contemplates contacting the product from step a) using a "water-immiscible organic solvent" following step a) or simultaneous with step a). The person skilled in the art knows numerous water-immiscible organic solvents that may be used according to the present invention. In a preferred embodiment, the term "water-immiscible organic solvent", as used herein, refers to a compound comprising at least two carbon atoms and having the tendency to form, in the presence of an aqueous liquid phase, preferably at 25° C., another liquid phase, which is clearly separate from the aqueous phase. The separate phase may be a continuous liquid phase or an emulsion. In another preferred embodiment, the term "water-immiscible", as used herein, refers to the tendency of a liquid compound not to be soluble in the water. Finally in another preferred embodiment, the term "water-immiscible", as used herein, means that a compound designated as such has a pH-value (J Sangster, *Octanol-Water Partition Coefficients: Fundamentals and Physical Chemistry*, Vol. 2 of *Wiley Series in Solution Chemistry*, John Wiley & Sons, Chichester, 1997) the decadic logarithm of which exceeds 0, preferably 0.5, more preferably 1 and most preferably 2. Preferred water-immiscible organic solvents comprise, but are not limited to water-immiscible solvents from the group comprising substituted and linear alkanes liquid at room temperature, cycloalkanes, cycloalkenes, aryls, fatty acids, fatty acid esters, alcohols, heterocycloalkanes, heterocycloalkenes and heteroaryls. The water-immiscible organic solvents may comprise more than one organic solvent. In a preferred embodiment, the term "extracting" a product using a "water-immiscible organic solvent", as used herein, means that the aqueous solution comprising the inventive cell is contacted with the water-immiscible organic solvent sufficiently long as to allow the product to enter the phase comprising the water-immiscible solvent. Subsequently, the phase comprising the water-immiscible organic solvent may be separated from the aqueous solution, for example by distillation or by decantation. Whether a compound is liquid or gaseous or neither, is preferably determined at 25° C. under atmospheric pressure.

In a preferred embodiment, the water-immiscible organic solvent is a fatty acid or an ester thereof, in a more preferred embodiment a fatty acid represented by the formula $CH_3$—$(CH_2)_x$—$COOR^S$, wherein x is 8, 9, 10, . . . , 28 and is more preferably 12 or more than 12, and wherein $R^S$ is H, or alkyl, the latter preferably methyl or ethyl. In another preferred embodiment, the water-immiscible organic solvent is an unsaturated fatty acid, preferably one having a carbon-carbon double bond at position 9 of the carbon chain, more preferably one having 12 carbon atoms or more. In a most preferred embodiment, the water-immiscible organic solvent is oleic acid. In another preferred embodiment, the water-immiscible solvent is hexanoic acid. In a preferred embodiment, the water-immiscible organic solvent is lauric acid methyl ester. The volume of the water-immiscible organic solvent is such that it is straightforward to separate it from the aqueous solution. In a preferred embodiment, the volume of the water-immiscible organic solvent is 2 to 98, more preferably 5 to 95, more preferably 10 to 40, most preferably 20 to 30 percent of the total combined volumes of aqueous solution and water-immiscible organic solvent.

In a preferred embodiment, the term "contacting", as used herein, means bringing about direct contact between alkyl and inventive cell such that the cell is able to take up and metabolise the alkyl. For example, the cell and the alkyl may not be in different compartments separated by a membrane such as an inorganic membrane. If the alkyl is solid or soluble, it may simply be added to the inventive cell in an aqueous solution. If the alkyl is gaseous, the aqueous solution comprising the cell may be sparged with a gas comprising said gaseous alkyl.

The term "an aqueous solution" comprises any solution that may be used to keep the inventive cell, at least temporarily, in a metabolically active and/or viable state and comprises, if such is necessary, any additional substrates. The person skilled in the art is familiar with numerous aqueous solution, usually referred to as media, that may be used to keep inventive cells, for example LB medium in the case of *E. coli*. In a preferred embodiment the aqueous solution is kept under aerobic conditions. It is advantageous to use as an aqueous solution a minimal medium, i.e. a medium of reasonable simple composition that comprises only the minimal set of salts and nutrients indispensible for keeping the cell in a metabolically active and/or viable state, by contrast to complex mediums. For example, M9 medium may be used as a minimal medium. If the alkyl to be oxidised has limited solubility in water, a detergent such as Tween or Triton may be added to the aqueous solution or a hydrophobic solvent may be used to solubilise the alkyl to be oxidised. The person skilled in the art is familiar with the preparation of various aqueous and organic solutions.

In a preferred embodiment, step b) is carried out following completion of the alkyl oxidation and preferably removal of the inventive cell from the aqueous solution. In a preferred embodiment, the alkyl oxidation, i.e. the oxidation of the alkyl catalysed by the inventive cell, may be regarded as complete if at least one of the following requirements is met: a) the inventive cell ceases to be metabolically active, b) there is no detectable substrate turnover c) there is no more substrate present in the aqueous solution d) the net amount of product does no longer increase significantly, for example if a concentration plateau has been reached or the slope of the graph indicating product formation is, over any period of two hours, zero or less. Cells may be removed from the aqueous solution in numerous ways known to the person skilled in the art, for example by centrifugation, filtration or decantation.

The invention is further illustrated by the following figures and non-limiting examples from which further features, embodiments, aspects and advantages of the present invention may be taken.

FIG. 1 shows different phase separation behaviour if ΔFadE mutant W3110 ΔFadE [alkB-alaD-TA] (left), also referred to as "ΔFadE", and strain W3110 [alkB-alaD-TA] (right), also referred to as wild type (WT), the latter identical to the former strain except for the fact that is FadE is not deleted, are used to produce ALSME. The arrow points the interphase between organic and aqueous phase visible after ten minutes in case the mutant is used. No such interphase is detectable after ten minutes in case the wild type strain is used.

Figure 1:

EXAMPLE 1: ACCELERATION OF SEPARATION OF A HYDROPHOBIC PHASE FROM AN AQUEOUS MEDIUM USING A CELL WITH REDUCED ACYL COA-DEHYDROGENASE ACTIVITY FOR THE PRODUCTION OF W-AMINO LAURIC ACID METHYL ESTER (ALSME)

The conversion of lauric acid methyl ester to w-amino lauric acid (ALS) methyl ester, via w-hydroxy lauric acid, was carried out in a parallel fermentation system comprising 8 vessels from DASGIP, using strains W3110 ΔFadE [alkB-alaD-TA] and W3110 [alkB-alaD-TA].

N. B. that these two strains comprise a pBR322-derived plasmid comprising oxidoreductase AlkB, an alcohol dehydrogenase and a transaminase in line with international application WO 2009/077461 and are identical except for the fact that the former has a deletion in the gene encoding FadE, the E. coli acyl-CoA dehydrogenase of the β-oxidation pathway.

1 liter reaction vessels were used for the fermentation. pH electrodes were calibrated by a two-point-calibration using pH 4 and pH 7 standard solutions. Reactors containing 300 mL tap water were autoclaved for 20 minutes at 121° C. Subsequently the pO2-detectors were polarized at the DAS-GIP system over night (for at least 6 hours). The next morning water was removed under a clean Bench and replaced by 300 mL of high cell density medium complemented with 100 mg/L ampicillin. Subsequently, pO2 detectors were subjected to one-point-calibration (stirrer: 400 rpm, gas flow: 10 sL/h air), and the tubings associated with the feed, correction agent and induction were cleaned by clean in Place using 70% ethanol, followed by 1 M NaOH, followed by rinsing with sterile VE water.

ALS and ALSME producing strains of E. coli were inoculated from the respective cryo cultures in LB medium (25 mL in a 100 mL flask with baffles) complemented with 100 mg/L ampicillin over night at 37° C. and 200 rpm for approximately 18 hours. Subsequently, 2 mL each of the cultures in high cell density medium (glucose 15 g/L (30 mL/L of a separately autoclaved 500 g/L stock solution comprising 1% $MgSO_4*7H_2O$ and 2.2% $NH_4Cl$), $(NH_4)_2SO4$ 1.76 g/L, $K_2HPO_4$ 19.08 g/L, $KH_2PO_4$ 12.5 g/L, yeast extract 6.66 g/L, trisodium dihydrate 2.24 g/L, ammonium ter iron citrate solution: 17 mL/L of a separately autoclaved 1% stock solution, trace element solution: 5 mL/L of a separately autoclaved stock solution (HCl (37%) 36.50 g/L, $MnCl_2*4H_2O$ 1.91 g/L, $ZnSO_4*7H_2O$ 1.87 g/L, ethylenediamintetraacetic acid dihydrate 0.84 g/L, $H_3BO_3$ 0.30 g/L. $Na_2MoO_4*2H_2O$ 0.25 g/L, $CaCl_2*2H_2O$ 4.70 g/L, $FeSO_4*7H_2O$ 17.80 g/L, $CuCl_2*2H_2O$ 0.15 g/L)) (20 mL per strain in a 100 mL flask with bethels) with 100 mg/L ampicillin were inoculated and incubated at 37° C./200 rpm for another 5.5 hours.

The optical density of a culture at 600 nm was determined in the case of W3110 ΔFadE [alkB-alaD-TA] as 6.9 and 7.4 in the case of W3110 [alkB-alaD-TA]. In order to inoculate the reaction vessels to a final optical density of 0.1, 4.0 mL or 4.4 mL, respectively, were transferred into a 5 mL syringe under sterile conditions and used to inoculate the reaction using a hollow needle and a septum covered by a layer of 70% ethanol. The following standard program was used

| | DO-controller | | pH-controller | |
|---|---|---|---|---|
| Preset | 0% | Preset | 0 ml/h |
| P | 0.1 | P | 5 |
| Ti | 300 s | Ti | 200 s |
| Min | 0% | Min | 0 mlL/h |
| Max | 100% | Max | 40 mL/h |

| N (Rotation) | from | to | XO2 (I gas mixture) | from | to | F (gas flow) | from | to |
|---|---|---|---|---|---|---|---|---|
| growth and biotransformation | 0% 400 rpm | 30% 1500 rpm | growth and biotransformation | 0% 21% | 100% 21% | growth and biotransformation | 15% 6 sL/h | 80% 72 sL/h |

| | |
|---|---|
| script | |
| trigger sharp | 31% DO (1/60 h) |
| induction IPTG | 2 h after feed start |
| feed trigger | 50% DO |
| feed rate | 3 [mL/h] |

The experiment carried out falls into to phases: the growth phase, wherein the aim is to attain cells at a certain optical density, and the subsequent biotransformation phase, wherein the aim is to convert the substrate lauric acid methyl ester to w-amino lauric acid methyl ester. pH values were maintained at 6.8 using ammonia (12.5%). During culture and biotransformation the dissolved oxygen in the culture was maintained via the stirrer and the gas flow rate at 30%. The fermentation was carried out as a fed batch, wherein the feed start, 5 g/Lh glucose feed (500 g/L glucose comprising 1% $MgSO_4*7H_2O$ and 2.2% $NH_4Cl$), was triggered by a DO-Peak. At the time of feed start the temperature was lowered from 37° C. to 30° C. Expression of the transaminase was induced by automatic addition of IPTG (1 mM) 2 h after feed start. alk-genes were induced by manual addition of DCPK (0.025% v/v) 10 h after feed start. The optical density of the culture broth was determined prior to starting the biotransformation.

The biotransformation phase was started 14 h after feed start by adding as a batch a mixture comprising lauric acid methyl ester and oleic acid (technical grade, 90%) to the fermentation broth. In order to provide an amino group donor for the transaminase, half an hour prior to start of the biotransformation 5 mL of a 3M ammonium sulfate solution was added to the fermentation broth. 2 mL fermentation broth samples were removed from the vessel and part of it was diluted 1:20 in a mixture comprising acetone and HCl (c(HCl) 0.1 mol/L) and extracted. Samples were taken 1, 2, 3, 4, 5, 7.5, 10.5, 19.5 and 21 h following start of the biotransformation from all reaction vessels. Oxygen transfer rate (OTR) and carbon transfer rate (CTR) were determined during the fermentation via analysis of exhaust gas from the DASGIP systems. Fermentation was terminated 21 h after start of the biotransformation. The stirrer, the gas flow, the temperature control and pH control were switched of and the vessel was given the opportunity to settle for another 5-10 minutes.

Figure 3:
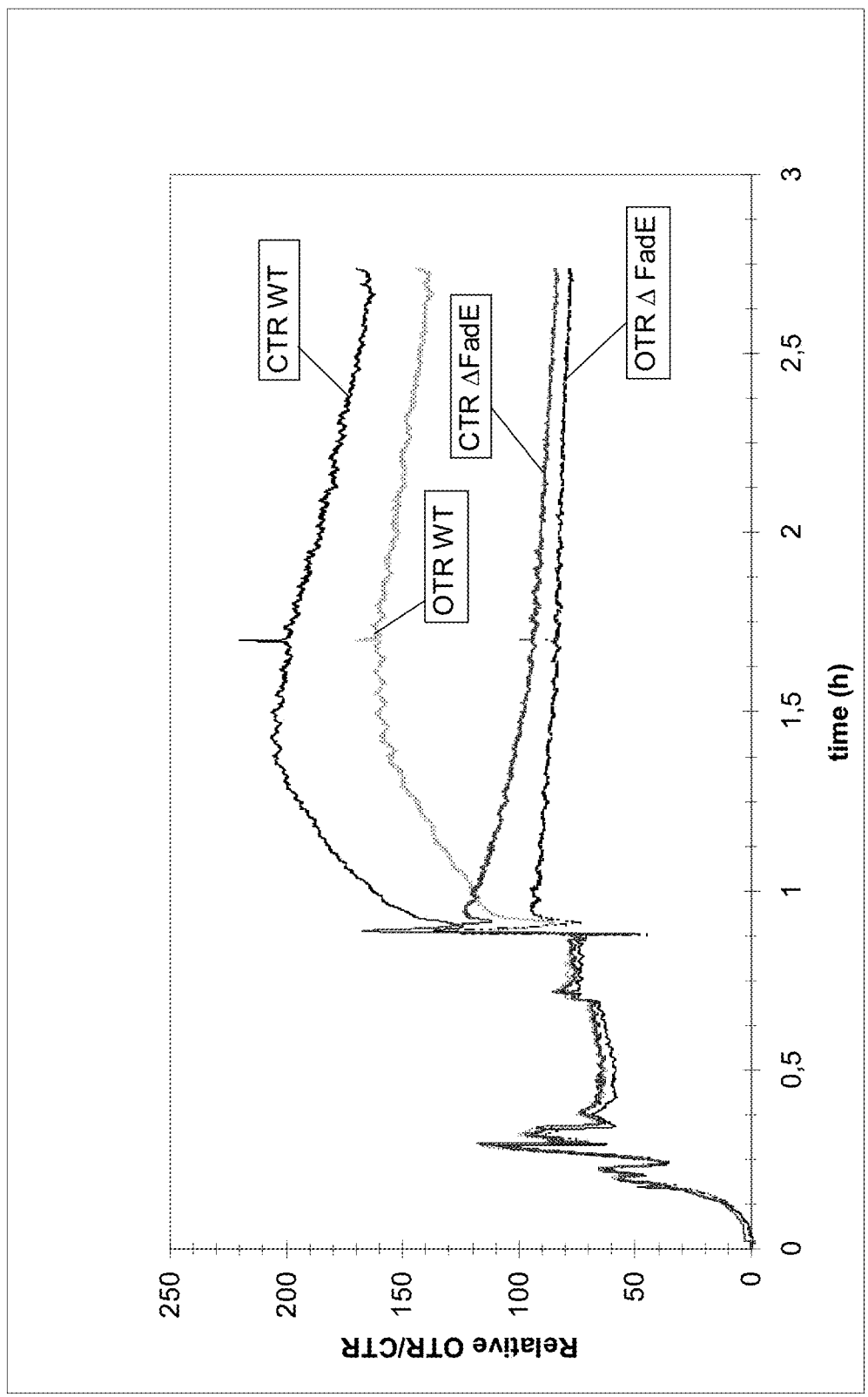
FIG. 3 shows the oxygen transfer rate and the carbon dioxide transfer rate of both strains used for the experiment described with respect to FIG. 1.
Figure 4:
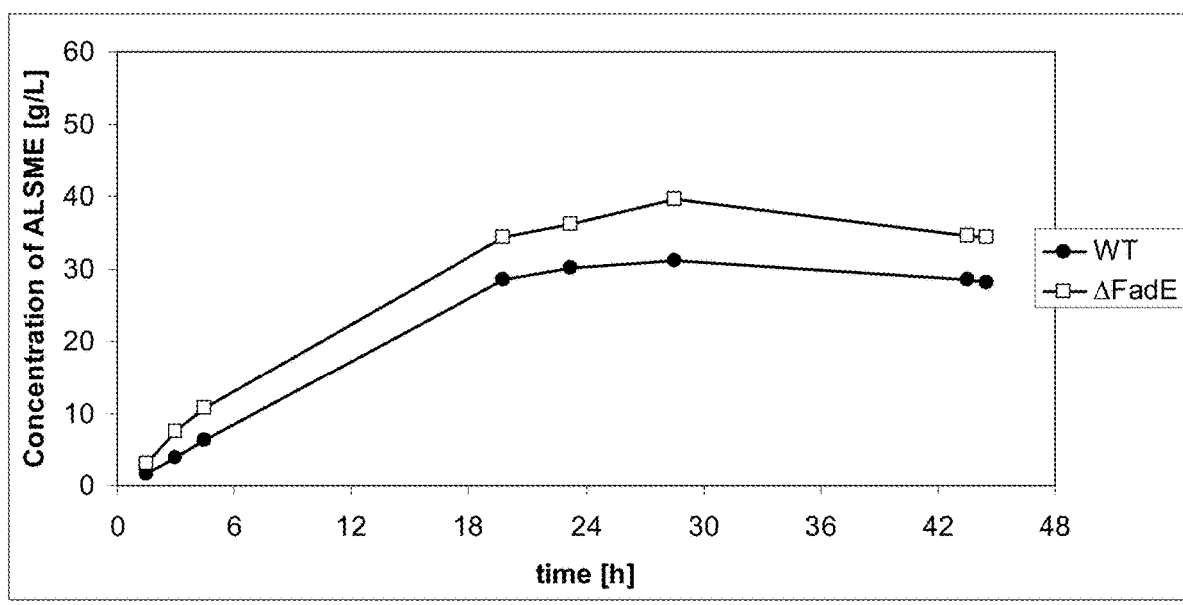
FIG. 4 shows the concentrations of ALSME over time in the same experiment described with respect to FIG. 1.

Results:

As the biotransformation progresses, the oxygen and carbon transfer rates increase significantly in the case of W3110 [alkB-alaD-TA]. By contrast the oxygen and carbon transfer rates decrease in the case of the deletion mutant W3110 ΔFadE [alkB-alaD-TA] and approach the level observed prior to the biotransformation (FIG. 3). The amount of product formed by both strains is comparable (FIG. 4), in fact the yield is slightly better in case the mutant is used.

Figure 2:
FIG. 2 shows the results of the same experiment as described with respect to FIG. 1, except for the fact that the medium was transferred to Falcon tubes after completion of the fermentation.

10 minutes after completion of the biotransformation a clear phase separation could be visually detected in the reaction vessel comprising the strain W3110 ΔFadE [alkB-alaD-TA], wherein the upper phase comprised approximately 40% and the bottom phase comprised approximately 60% of the volume. A thin inter phase could be observed between the phases. Samples were taken from the upper and lower phase, transferred into a 15 mL falcon tube and spun down at 5500×g for 10 minutes. The tube comprising the sample from the lower phase comprised approximately 95% aqueous phase and biomass. The tube comprising the sample from the upper phase comprised approximately 60% organic solution (FIG. 2). The reaction vessel comprising strain W3110 [alkB-alaD-TA] contained a homogenous emulsion after 10 minutes, and no phase separation could be observed for another 20 minutes (FIG. 1).

In summary, deletion of the gene encoding FadE, the *E. coli* acyl-CoA dehydrogenase of the β-oxidation pathway, leads to an improved phase separation if the mutant is in an aqueous solution and contacted with a water-immiscible organic solvent as well as to a lower consumption of oxygen.

The invention claimed is:

1. A method for oxidizing an alkyl, comprising:
   a) contacting the alkyl with an aqueous solution comprising a microorganism such that the alkyl is converted to an oxidized alkyl, where the microorganism expresses a recombinant alkane oxidase and has a reduced fatty acid degradation capacity compared to its wild type, wherein the fatty acid degradation capacity is reduced by deletion, inhibition or inactivation of a gene encoding an enzyme involved in the β-oxidation pathway;
   b) contacting the aqueous solution from a) with a water-immiscible organic solvent and
   c) allowing the aqueous solution contacted with the water-immiscible organic solvent from b) to settle for 5 to 10 minutes, thereby forming an aqueous phase comprising the microorganism and an organic phase comprising the water-immiscible organic solvent,
   wherein the alkyl is a compound represented by the formula H—$(CH_2)_x$—R, wherein x is at least 8, and R is selected from the group comprising —OH, —COH, —COOH, —COOR$^1$, —NH$_2$, —NO$_2$, —CN, —OPO$_3$H, —SO$_3$H and —H wherein R$^1$ is methyl or ethyl, and
   wherein the expressed recombinant alkane oxidase is AlkB from *Pseudomonas putida* GPo1 comprising the sequence of SEQ ID NO: 1 or a variant thereof having at least 90% identity to SEQ ID NO: 1, and
   wherein the enzyme involved in the β-oxidation pathway is selected from the group consisting of:
      a fatty acid importer comprising the sequence of SEQ ID NO: 2 or a variant thereof having at least 90% identity to SEQ ID NO: 2,
      a fatty acid-CoA ligase comprising the sequence of SEQ ID NO: 3 or a variant thereof having at least 90% identity to SEQ ID NO: 3,
      an acyl-CoA dehydrogenase comprising the sequence of SEQ ID NO: 4 or a variant thereof having at least 90% identity to SEQ ID NO: 4,
      an enoyl-CoA hydratase comprising the sequence of SEQ ID NO: 5 or a variant thereof having at least 90% identity to SEQ ID NO: 5, and
      a 3-ketoacyl-CoA thiolase comprising the sequence of SEQ ID NO: 6 or a variant thereof having at least 90% identity to SEQ ID NO: 6.

2. The method according to claim 1, wherein b) is carried out following completion of oxidation of the alkyl.

3. The method according to claim 1, wherein the alkyl is a linear alkane.

4. The method according to claim 1, wherein the water-immiscible organic solvent is a water-immiscible fatty acid or fatty acid ester.

5. The method according to claim 1, wherein the microorganism is a bacterial cell.

6. The method according to claim 1, wherein the microorganism is *E. coli*.

7. The method according to claim 1, wherein x in the formula H—$(CH_2)_x$—R is 11 or more.

8. The method according to claim 1, wherein the water-immiscible organic solvent is a fatty acid represented by the formula:

$$CH_3\text{—}(CH_2)_y\text{—}COOR^S,$$

wherein y is an integer from 8 to 28, and R$^S$ is H, or alkyl.

9. The method according to claim 1, wherein the water-immiscible organic solvent is lauric acid methyl ester.

10. The method according to claim 1, wherein the enzyme involved in the β-oxidation pathway is a fatty acid importer comprising the sequence of SEQ ID NO: 2 or a variant thereof having at least 90% identity to SEQ ID NO: 2.

11. The method according to claim 1, wherein the enzyme involved in the β-oxidation pathway is a fatty acid-CoA ligase comprising the sequence of SEQ ID NO: 3 or a variant thereof having at least 90% identity to SEQ ID NO: 3.

12. The method according to claim 1, wherein the enzyme involved in the β-oxidation pathway is an acyl-CoA dehydrogenase comprising the sequence of SEQ ID NO: 4 or a variant thereof having at least 90% identity to SEQ ID NO: 4.

13. The method according to claim 1, wherein the enzyme involved in the β-oxidation pathway is an enoyl-CoA hydratase comprising the sequence of SEQ ID NO: 5 or a variant thereof having at least 90% identity to SEQ ID NO: 5.

14. The method according to claim 1, wherein the enzyme involved in the β-oxidation pathway is a 3-ketoacyl-CoA thiolase comprising the sequence of SEQ ID NO: 6 or a variant thereof having at least 90% identity to SEQ ID NO: 6.

15. The method according to claim 1, wherein R in the formula H—$(CH_2)_x$—R is selected from the group consisting of —OH, —COH, —NH$_2$, —NO$_2$, —CN, —OPO$_3$H, —SO$_3$H and —H.

16. The method according to claim 1, wherein the water-immiscible organic solvent comprises at least one selected from the group consisting of oleic acid and hexanoic acid.

17. The method according to claim 1,
   wherein the alkyl comprises lauric acid methyl ester.

18. The method according to claim 1,
   wherein the alkyl comprises lauric acid methyl ester, and
   wherein the enzyme involved in the β-oxidation pathway is an acyl-CoA dehydrogenase comprising the sequence of SEQ ID NO: 4 or a variant thereof having at least 90% identity to SEQ ID NO: 4.

19. The method according to claim 1,
   wherein the alkyl comprises lauric acid methyl ester,
   wherein the water-immiscible organic solvent comprises oleic acid, and
   wherein the enzyme involved in the β-oxidation pathway is an acyl-CoA dehydrogenase comprising the sequence of SEQ ID NO: 4 or a variant thereof having at least 90% identity to SEQ ID NO: 4.

20. The method according to claim 19, wherein the organic phase further comprises ω-amino lauric acid methyl ester.

* * * * *